United States Patent
Rowland et al.

(10) Patent No.: US 11,691,018 B2
(45) Date of Patent: Jul. 4, 2023

(54) USING IMPLANTABLE MEDICAL DEVICES TO AUGMENT NONINVASIVE CARDIAC MAPPING

(71) Applicant: CARDIOINSIGHT TECHNOLOGIES, INC., Independence, OH (US)

(72) Inventors: William Rowland, Murrayville, GA (US); Timothy G. Laske, Shoreview, MN (US); Qing Lou, Solon, OH (US); Qingguo Zeng, Solon, OH (US)

(73) Assignee: CARDIOINSIGHT TECHNOLOGIES INC., Independence, OH (US)

( * ) Notice: Subject to any disclaimer, the term of this patent is extended or adjusted under 35 U.S.C. 154(b) by 27 days.

(21) Appl. No.: 17/179,465

(22) Filed: Feb. 19, 2021

(65) Prior Publication Data
US 2022/0266009 A1     Aug. 25, 2022

(51) Int. Cl.
*A61B 5/367*     (2021.01)
*A61N 1/365*     (2006.01)
(Continued)

(52) U.S. Cl.
CPC ............. *A61N 1/365* (2013.01); *A61B 5/063* (2013.01); *A61B 5/287* (2021.01); *A61B 5/367* (2021.01);
(Continued)

(58) Field of Classification Search
CPC ................................ A61N 1/365; A61B 5/367
(Continued)

(56) References Cited

U.S. PATENT DOCUMENTS

| 5,687,737 A | 11/1997 | Branham et al. |
| 7,308,297 B2 | 12/2007 | Reddy et al. |

(Continued)

FOREIGN PATENT DOCUMENTS

| WO | 2007/017879 A2 | 2/2007 |
| WO | 2016033599 A1 | 3/2016 |
| WO | 2016196793 A1 | 12/2016 |

OTHER PUBLICATIONS

T. F. Oostendorp and A. Van Oosterom; "The surface Laplacian of the potential: theory and application," in IEEE Transactions on Biomedical Engineering, vol. 43, No. 4; doi: 10.1109/10.486259; Apr. 1, 1996, 12 pgs.

(Continued)

*Primary Examiner* — Nicole F Lavert
(74) *Attorney, Agent, or Firm* — Tarolli, Sundheim, Covell & Tummino, LLP

(57) ABSTRACT

An example method includes establishing a communications link between an electrophysiology (EP) monitoring system and an implantable medical device (IMD). IMD electrical data is received at the monitoring system via the communications link. The IMD electrical data may be synchronized with EP measurement data to provide synchronized electrical data based on timing of a synchronization signal sensed by an IMD electrode and/or EP electrodes. The method also includes computing reconstructed electrical signals for locations on a surface of interest within the patient's body based on the synchronized electrical data and geometry data. The geometry data represents locations of the EP electrodes, a location of the IMD electrode within the patient's body and the surface of interest.

28 Claims, 8 Drawing Sheets

(51) Int. Cl.
- *A61M 60/178* (2021.01)
- *A61B 5/287* (2021.01)
- *A61B 5/06* (2006.01)
- *A61B 5/00* (2006.01)
- *A61N 1/05* (2006.01)
- *A61N 1/372* (2006.01)

(52) U.S. Cl.
CPC ............ *A61B 5/4836* (2013.01); *A61B 5/686* (2013.01); *A61M 60/178* (2021.01); *A61N 1/0563* (2013.01); *A61N 1/37235* (2013.01); *A61B 2560/0223* (2013.01)

(58) Field of Classification Search
USPC .............................................................. 607/7
See application file for complete search history.

(56) References Cited

U.S. PATENT DOCUMENTS

| | | | |
|---|---|---|---|
| 7,313,433 B2 | 12/2007 | Yu et al. | |
| 7,529,584 B2 | 5/2009 | Laske et al. | |
| 8,391,975 B2 | 3/2013 | Corbucci | |
| 9,155,897 B2 | 10/2015 | Ghosh et al. | |
| 10,532,213 B2 | 1/2020 | Ghosh | |
| 2005/0149138 A1* | 7/2005 | Min | A61N 1/3627 607/27 |
| 2007/0055124 A1 | 3/2007 | Viswanathan et al. | |
| 2007/0153815 A1* | 7/2007 | She | H04L 69/18 370/466 |
| 2008/0177344 A1 | 7/2008 | Maskara et al. | |
| 2009/0053102 A2 | 2/2009 | Rudy et al. | |
| 2009/0099619 A1 | 4/2009 | Lessmeier et al. | |
| 2010/0106224 A1* | 4/2010 | Von Arx | A61N 1/37223 607/60 |
| 2011/0054264 A1* | 3/2011 | Fischell | G16H 40/67 600/300 |
| 2013/0184697 A1* | 7/2013 | Han | A61B 90/37 606/32 |
| 2015/0164357 A1* | 6/2015 | Zeng | A61B 5/7278 607/18 |
| 2015/0216438 A1 | 8/2015 | Bokan et al. | |
| 2016/0242663 A1* | 8/2016 | Jayan | A61B 5/318 |
| 2019/0282112 A1* | 9/2019 | Jia | A61B 5/349 |
| 2021/0106832 A1 | 4/2021 | Ghosh et al. | |

OTHER PUBLICATIONS

Kaplonek, W., Nadolny, K., & Królczyk, G. M.; "The Use of Focus-Variation Microscopy for the Assessment of Active Surfaces of a New Generation of Coated Abrasive Tools"; Measurement Science Review, 16(2), doi: https://doi.org/10.1515/msr-2016-0007; May 6, 2016; 12 pgs.

University of Pittsburgh—Of the Commonwealth System of Higher Education; "Electrocardiogram reconstruction from implanted device electrograms"; May 24, 2012; 26 pgs.

G. Stuart Mendenhall, Samir Saba; "12-lead surface electrocardiogram reconstruction from implanted device electrograms"; EP Europace, vol. 12, Issue 7, Jul. 2010, , https://doi.org/10.1093/europace/euq115; Published Apr. 21, 2010; 9 pgs.

Applicant: Cardioinsight Technologies, Inc.; "Using Implantable Medical Devices to Augment Noninvasive Cardiac Mapping"; International Application No. PCT/US2022/015028 Filed Feb. 3, 2022; Authorized Officer: T. Artikis; May 11, 2022; 11 pgs.

* cited by examiner

USING IMPLANTABLE MEDICAL DEVICES TO AUGMENT NONINVASIVE CARDIAC MAPPING

TECHNICAL FIELD

This disclosure relates to using implantable medical devices to augment noninvasive cardiac mapping.

BACKGROUND

Electrocardiographic imaging (ECGI) is a noninvasive multi-lead ECG-type imaging tool that combines noninvasive electrical measurements with three-dimensional geometry of the heart and torso to reconstruct electrical signal onto the heart or another surface. Mathematically, this is performed by solving the inverse problem. However, the inverse solution is ill-posed such that inaccuracies in the measured electrical signals can result in significant errors.

SUMMARY

This disclosure relates to using implantable medical devices to augment cardiac mapping, which may include noninvasive and/or invasive cardiac mapping.

As one example, a method includes establishing a communications link between a cardiac monitoring system and an implantable medical device (IMD). The IMD includes one or more IMD electrodes. IMD electrical data is received at the monitoring system via the communications link. The IMD electrical data is synchronized with electrical measurement data to provide synchronized electrical data based on timing of a synchronization signal sensed by an IMD electrode and/or electrophysiology electrodes. The method also includes computing reconstructed electrical signals for locations on at least one surface of interest within the patient's body based on the synchronized electrical data and geometry data. The geometry data may represent locations of the electrophysiology electrodes, a location of the IMD electrode within the patient's body and the surface of interest.

As another example, a system includes an implantable medical device (IMD) comprising an IMD electrode or electrodes adapted to be positioned within a patient's body. The IMD includes circuitry to receive and interpret IMD electrical data sensed by an IMD electrode or series of electrodes. In some examples, the IMD uses these electrical signals to determine whether therapeutic pulses or shocks are require in order to manage the patient's rhythm. Additionally, or alternatively, the IMD may also be used as a monitoring device to store electrical signals for later interpretation by a physician. The system also includes a monitoring system. The monitoring system includes non-transitory memory and a processor. The memory may store the IMD electrical data, monitoring electrical data and geometry data. The monitoring electrical data may represent signals measured by monitoring electrodes, which may include body surface electrodes distributed on a surface of the patient's body and/or one or more invasive electrodes within the patient's body. The processor is coupled to the memory to access data and instructions stored in the memory. The instructions may be programmed to establish a communications link between the monitoring system and the IMD and receive the IMD electrical data through the communications link. The instructions also synchronize the IMD electrical data and the monitoring electrical data to provide synchronized electrical data based on timing of a synchronization signal sensed by the IMD electrode and/or the monitoring electrodes. Reconstructed electrical signals can be reconstructed for locations residing on a surface of interest based on the synchronized electrical data and the geometry data. In another example, the monitoring electrical data may include electrical measurement data from an invasive electroanatomic mapping system that may be combined with the information from the IMD to further refine the electrical maps.

DETAILED DESCRIPTION

Figure 1:
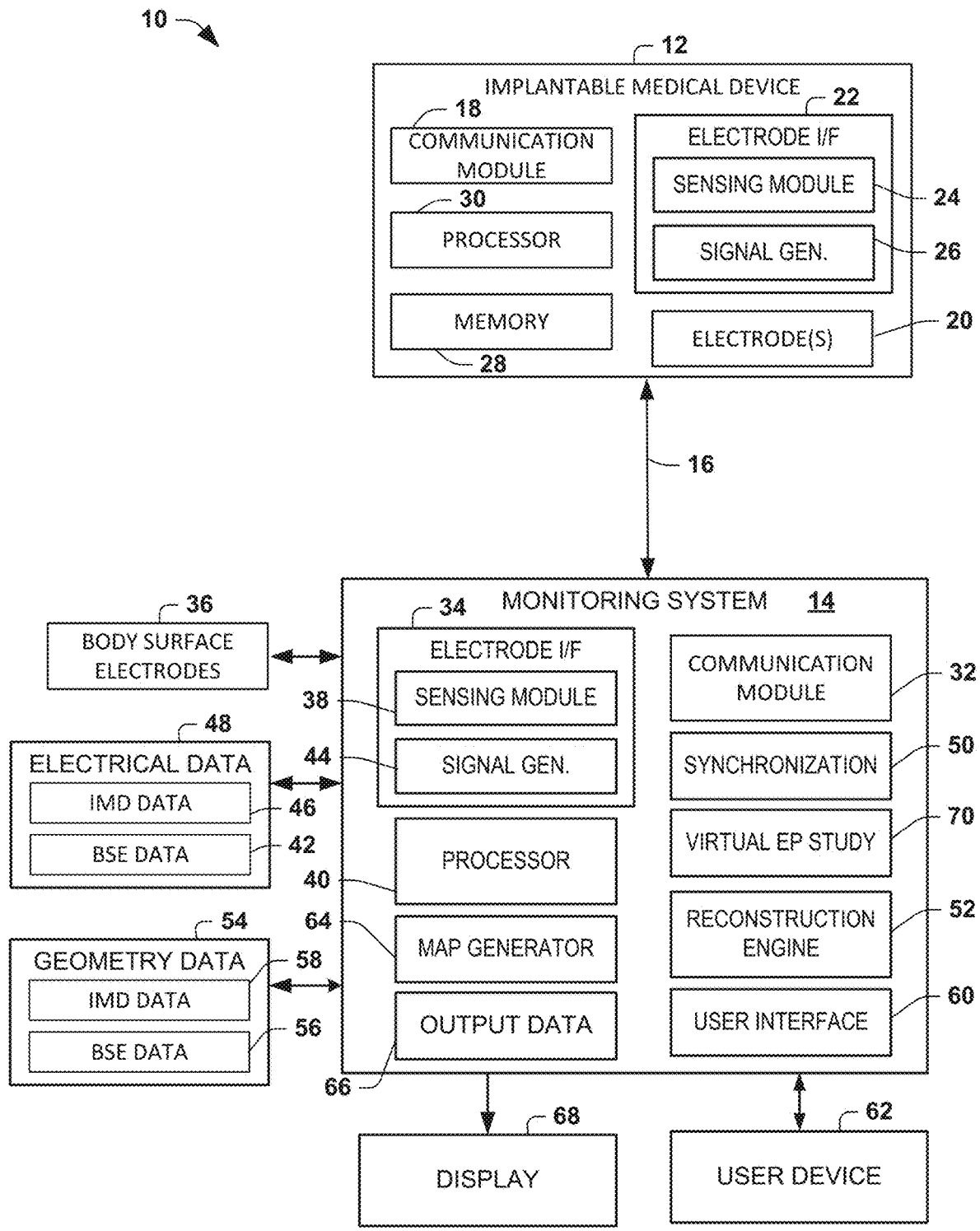
FIG. 1 depicts an example system that includes an implantable medical device and electrophysiology monitoring system.

This disclosure relates to using implantable medical devices to augment electrophysiology mapping. An example system includes an implantable medical device (IMD) and an electrophysiology monitoring system. The implantable medical device includes one or more IMD electrodes adapted to be positioned at a location within a patient's body. The implantable medical device including circuitry (e.g., analog and/or digital circuitry) to provide IMD electrical data based on an electrical signal sensed by the IMD electrode and to deliver a stimulus signal through the IMD electrode.

The monitoring system may be implemented as a computer system that includes non-transitory memory to store data, which may include IMD electrical data from the IMD and electrophysiology (EP) electrical data and geometry data. The EP electrical data may include noninvasive electrical measurement data representing noninvasive electrical activity measured noninvasively from surface locations on the patient's body. Additionally or alternatively, the EP electrical data may include invasive electrical measurement data representing electrical activity measured noninvasively within the patient's body. The geometry data may represent the EP measurement locations, the IMD sensing location(s) as well patient anatomy in three-dimensional space. The monitoring system also includes a processor coupled to the memory to access the data and instructions stored in the memory to perform functions disclosed herein. For example, the instructions are programmed to establish a communications link between the processor and the implantable medical device. The communications link may be a direct link or an indirect link through another device, such as a programmer, and may be bidirectional.

The processor is also programmed to determine timing of a synchronization signal as sensed by at least one electrode of the IMD and/or at least some EP electrodes, which are reflected in the EP electrical data. The synchronization signal may be provided by one or more electrodes at a location within a patient's body (e.g., by the IMD electrode) and/or an EP measurement location (e.g., by a body surface electrode or an invasive electrode). An EP map may be determined for respective locations residing on a surface (or surfaces) of interest based on the IMD electrical data, the EP electrical data (e.g., noninvasive and/or invasive electrical measurements), the geometry data and the timing of the synchronization signal.

In some examples, the IMD electrical data and geometry data associated with the IMD electrode(s) may be used to determine one or more boundary conditions. The boundary condition may be used by the reconstruction engine to constrain an inverse solution that is utilized to reconstruct the electrical signal on the cardiac envelope.

Additionally, or alternatively, the monitoring system may be programmed to control an impedance measurement method in which impedance is measured between the IMD electrode(s) and EP electrodes. For example the impedance may be measured based on one more signals (e.g., subthreshold or suprathreshold signals) that are generated at the IMD electrode(s) and/or EP electrodes. The impedance measurements may be used to characterize the conductivity of the tissue and fluids located within the patient's body between the IMD electrode(s) and EP electrodes on the body surface. The processor further may be programmed to generate or update model data representing an anatomic model, which is used to compute one or more EP maps on the surface of interest.

In view of the foregoing, by leveraging information from the IMD, the accuracy of reconstructed electrical signals themselves can be improved as well as improved EP mapping functions. For example, concurrent local and global assessments of cardiac tissue may be provided in a single EP map. Moreover, the bidirectional link between the IMD and the monitoring system enable closed loop control that can achieve new sensing paradigms in which signals usually measured by mapping catheters may be replicated and integrated into the electrical measurements data without requiring use of an actual catheter. Because, in some examples, the systems and methods may be implemented without use of an electrophysiology (EP) catheter the likelihood of inadvertently dislodging the IMD or its leads is mitigated.

FIG. 1 depicts an example of a system 10 for augmenting EP mapping. The system 10 includes an implantable medical device (IMD) 12 and a monitoring system 14 that are configured to communicate over a communication link 16. The communication link 16 may include one or more wireless and/or physical connections (e.g., electrical conductors, optical fibers). Useful examples of the implantable medical device include an implantable cardioverter-defibrillator, a pacemaker or a ventricular assist device. Some commercial examples IMDs that may be used as the IMD 12 include implantable cardioverter-defibrillator from Medtronic plc, such as including the Visia ICD system, the Evera ICD, the Crome system and the Cobalt System. Commercial examples of pacemakers and pacing systems that may be used to implement the IMD 12 include the Azure pacemaker, the Advisa pacing system, the Adapta pacemaker and any of the Micra transcatheter pacing systems, which are available from Medtronic plc. In other examples, different pacing systems may be used as the IMD 12.

In the example of FIG. 1, the IMD 12 includes a communications module 18 configured to communicate data (e.g., IMD data and instructions) through the communication link 16. For example, the communications module 18 can communicate through the link 16 with one or more devices including the monitoring system 14. The IMD 12 also includes one or more IMD electrodes 20. The electrodes may be mounted to a housing that contains the IMD 12. Additionally, or alternatively, the electrodes 20 may be mounted to one or more leads that may extend from the housing of the IMD. The number and placement of electrodes can vary depending upon the type of IMD that is being utilized for a given patient. In some examples, one or more IMD may be used concurrently for a given patient.

The IMD 12 also includes an electrode interface 22 having respective inputs coupled to each of the electrodes 20. The electrode interface 22 may include a sensing module 24 and a signal generator 26. For example, the sensing module 24 includes circuitry configured to measure electrical signals received at the electrodes 20. The electrode interface 22 thus can include analog or digital circuitry configured to receive, amplify and store the measured electrical signals, in memory 28. For example, a processor 30 is coupled to the electrode interface 22 to receive the electrical measurement data from the interface and store the data in the memory 28 as IMD electrical measurement data.

The processor 30 may include any one or more of a microprocessor, a controller, a digital signal processor (DSP), an application specific integrated circuit (ASIC), a field-programmable gate array (FPGA), or equivalent discrete or integrated logic circuitry. In some examples, processor 30 may include multiple components, such as any combination of one or more microprocessors, one or more controllers, one or more DSPs, one or more ASICs, or one or more FPGAs, as well as other discrete or integrated logic circuitry. The term "processor" "processor module" or "processing circuitry" may generally refer to any of the foregoing logic circuitry, alone or in combination with other logic circuitry, or any other equivalent circuitry.

The signal generator 26 includes circuitry configured to deliver an electrical signal to one or more respective IMD electrodes 20 based on electrical parameters defined for the signal (e.g., pulse amplitude, pulse duration and frequency). The electrical signal may be a stimulus signal that may be subthreshold or super threshold. As used herein, the "subthreshold" refers to a signal that is sufficiently large to be measurable by one or more electrodes above baseline noise that is detected by such electrodes, but that is not so large as to stimulate cardiac conduction (i.e., trigger an action potential to pace the heart). In contrast, suprathreshold refers to a signal that is sufficient to stimulate cardiac conduction. In an example, the signal generator 26 may provide a signal to one or more of the electrodes 20 to perform pacing. For example, the processor 30 is programmed to control the signal generator to provide the electrical stimulus signal to one or more electrodes such as to implement cardioversion, pacing or defibrillation.

In some examples, the processor is configured to monitor the measurement signals from the sensing module 24 and to control the signal generator 26 to provide a suprathreshold stimulus signal responsive to the sensed measurement signals. Thus the IMD 12 may be implemented as a self-contained system such as implantable within the patient's body so that the one or more electrodes are provided at desired locations according to the type of stimulus to be provided to the patient's heart, such as to perform cardioversion and/or defibrillation.

The monitoring system 14 includes a communications module 32 that is configured to communicate with the implantable medical device 12 through the communication link 16. As described, the communication link 16 may be direct communication with the implantable medical device or may be an indirect communication to one or more other devices (not shown). The communications module 32 may include communications circuitry configured to communicate using one or more forms of communication.

The monitoring system 14 also includes an electrode interface 34 that is coupled to EP electrodes 36. In one example, the electrode interface 34 may be coupled to an arrangement of EP electrodes 36 through respective electrically conductive leads. In other examples, the EP electrodes may be coupled to the electrode interface 34 through other forms of communication (e.g., optical fiber or wireless leads). In an example, the EP electrodes are implemented as body surface electrodes to be distributed non-invasively across a patient's body surface. In an additional or alternative example, the EP electrodes are implemented as electrodes configured for invasively measuring electrophysiology signals, such as mounted to a catheter or other instrument that is moveable within a patient's body.

The electrode interface 34 includes a sensing module 38 having circuitry (e.g., amplifier and/or filters) configured to receive signals measured by the respective EP electrodes 36 and provide corresponding electrical measurement signals. The monitoring system 14 may also include a processor 40. The processor 40 may be similar in design and operation to the processor 30 described above. The processor 40 is configured to execute instructions to perform various control and processing functions disclosed herein (e.g., executable functions 50, 52, 60, 70 and 64).

In an example, the processor 40 includes a signal processing function to process the received measurement signals from the EP electrodes 36 and convert the signals to corresponding body surface electrical data (EP data 42). Alternatively, the electrode interface 34 may be configured convert the measurement signals to respective EP data 42. The signal processor 40 may be implemented as hardware and/or software, such as including a digital signal processor and other processing circuitry to remove noise and convert the received signals into a desired format for the EP data 42. This can include adding channel information, adding timestamps, line noise removal or other signal processing functions that may be desired.

In some examples, the electrode interface 34 also includes a signal generator 44. The signal generator 44 includes circuitry configured to generate one or more signals that are supplied to respective EP electrodes 36. For example, the signal generator 44 may generate a pulse or other types of signals to one or more of the EP electrodes 36 that may be detected by other EP electrodes and/or the IMD electrode(s) 20.

As described above, the monitoring system 14 may receive IMD electrical data from the IMD 12 (e.g., as encoded data) through the communications link 16. The communications module 32 can decode the signal and extract the IMD data and store such data in memory data as IMD electrical data 46. The EP data 42 and IMD data 46 collectively form electrical data 48 that is stored in memory (e.g., local and/or remote memory) of the monitoring system 14. For example, the IMD electrical data 46 includes data representing signals generated and/or measured by the IMD electrodes 20. The IMD data 46 may also include an electrode identifier that specifies which electrode the data is associated with and include local timing information for the IMD 12.

In the example of FIG. 1, the monitoring system 14 also includes a synchronization function 50 such as may be implemented as machine-readable instructions executable by a processor of the monitoring system. The synchronization function 50 may control one or more signal generators 44 and 26 to generate a synchronization signal via respective electrodes 20 or 36. The synchronization signal may be a subthreshold signal or a suprathreshold signal. In response to the synchronization signal, one or both sensing modules 24 and 38 measure electrical signals and provide electrical measurement signals that may be stored in memory of the monitoring system as respective IMD electrical data 46 and BSE electrical data 42, as described above.

The synchronization function 50 is programmed to synchronize the IMD electrical data 46 and the EP data 42 based on a timing of the synchronization signal that is sensed by one or more of the electrodes 20 and 36 and provided as part of the electrical data. For example, the synchronization functions are programmed to setting a zero or other common start time for an identified feature (e.g., peak of the pulse, bottom of the pulse, rising edge, falling edge) of the synchronization pulse. The zero or other start time thus is used to align the data in time so that the identified data feature is at the alignment time for each of the measurement channels. Alternatively, a timing offset may be determined for each of the channels and utilized to adjust the timing of the electrical data 46 and the EP data 42 according to the timing offset.

As a further example, the synchronization function 50 is programmed to control the signal generator of the IMD 12 through the communications link 16 to generate the synchronization signal through one or more of the IMD electrodes 20. For example, the synchronization function 50 issues synchronization control instructions through the communications module 32 that are communicated via the link 16 to the IMD 12. The communications module 18 decodes the received signal and the processor 30 is configured to execute the instructions and thereby control the signal generator 26 to deliver the synchronization pulse to one or more respective electrodes 20 responsive to the instructions. The synchronization function 50 further instructs the sensing module 38 to measure electrical activity by the EP electrodes 36 (e.g., on and/or within the patient's body) responsive to the synchronization signal (generated by electrodes 20). The sensing module 24 also may measure signals from one or other IMD electrodes 20 to generate IMD data.

The synchronization function 50 further may control the signal processor 40 to analyze the measured electrical activity data (e.g., stored at EP data 42 and/or IMD data 46) to identify a feature of the synchronization signal reflected in the measured electrical signals corresponding to the stored electrical data 48. The identified feature can be any signal, such as signal morphology and/or timing, which may manifest in the signals being measured by the electrodes 36 or derived from the measured signals (e.g., peak of the pulse, bottom of the pulse, rising edge, falling edge, frequency and the like). The synchronization function 50 thus may utilize the identified feature to synchronize the IMD data 46 with the EP data 42.

As another example, the synchronization function 50 is programmed to control the signal generator 44 to generate a synchronization signal via one or more of the EP electrodes 36. As described herein, the EP electrodes 36 may include body surface electrodes for a non-invasive EP system and/or invasive electrodes for an invasive EP system. The synchronization function 50 may employ the communications module 32 to receive IMD synchronization data via the communications link 16. The IMD synchronization data thus may represent electrical signals measured by one or more respective IMD electrodes 20 responsive to the synchronization signal generated by one or more of the EP electrodes 36. In some examples, the synchronization function 50 may provide instructions to the IMD 12 such that the processor 30 activates signal generator 26 to measure electrical signals using one or more IMD electrodes 20 during the synchronization signal that is generated on the body surface. The received synchronization data may be stored as part of the IMD electrical data 46. The synchronization function 50 may employ the signal processor 40 to analyze the electrical activity of the IMD synchronization data to identify a feature of the synchronization signal that is reflected in the measured signal, as described above. The synchronization function thus synchronizes the IMD data 46 and the EP data 42 based on the identified feature. The synchronized data may be analyzed and further processed to augment or enhance the functions of the monitoring system. In some examples, the IMD data 46 or the EP data 42 amplitude may be adjusted to a common scale (e.g., a normalized scale) to facilitate analysis and processing of the synchronized electrical data 48.

For example, the synchronization function 50 can synchronize the IMD data 46 and EP data 42 for a given time interval of the measured electrical signals. For subsequent intervals, the synchronization function 50 may recompute the synchronization between the respective signals represented by the IMD data 46 and EP data 42 for the respective intervals. In some examples, the synchronization function 50 is programmed to periodically or intermittently generate a synchronization signal (e.g., internally via one or more of the IMD electrodes 20 and/or externally via one or more of the EP electrodes 36) and align the electrical data 42 and 46 to maintain accurate synchronization among such data for subsequent analysis and reconstruction by the reconstruction engine 52. This is especially useful to ensure accuracy is sustained during lengthy electrophysiological studies.

The monitoring system 14 may also include a reconstruction engine 52 (e.g., instructions) programmed to compute reconstructed electrical signals for locations on a surface of interest within the patient's body. In one example, the reconstruction engine 52 computes the reconstructed signals (e.g., electrical potentials) on the surface of interest by executing instructions (an algorithm) to combine electrical signals spatially and temporally based on geometry data 54 and the electrical data (e.g., EP data 42 and IMD data 46). In another example, the reconstruction engine 52 computes the reconstructed signals (e.g., electrical potentials) on the surface of interest by executing instructions (an algorithm) to solve the inverse problem based on geometry data 54 and the synchronized electrical data (e.g., EP data 42 that has been synchronized with IMD data 46). Examples of inverse algorithms that can be implemented by the reconstruction engine 52 include those disclosed in U.S. Pat. Nos. 6,772,004, 7,983,743 and 9,980,660, each of which is incorporated herein by reference. The reconstruction engine 52 can calculate the reconstructed electrical signals on the surface of interest for one or more surfaces of interest over one or more time intervals. The time interval(s) may be selected through a user interface 60 in response to a user input entered by a user device 62 (e.g., mouse, keyboard, touchscreen interface, gesture interface or the like).

For example, the reconstruction engine 52 is programmed to calculate a transfer matrix based on the geometry data 54 and the synchronized electrical data. The reconstruction engine 52 further may employ a regularization technique to estimate values for the reconstructed electrical signals on the surface of interest, which is defined by the geometry data 54.

In the example of FIG. 1, the geometry data 54 includes EP data 56 representing three-dimensional locations of the EP electrodes 36 distributed across a patient's body. The geometry data also includes IMD data 58 representing locations of the IMD electrodes 20 within the patient's body. In some examples, the BSE geometry data and the IMD geometry data are derived from a common source (e.g., three-dimensional image set or a navigation system), which helps to further improve the accuracy of the relative three-dimensional position of the electrodes 20 and 36 as well as the resulting reconstructed signals. The geometry data 54 also includes data representing the surface (or surfaces) of interest in three-dimensional space. For example, the surface of interest is a cardiac envelope, such as an epicardial surface, an endocardial surface, a combination of epicardial and endocardial surfaces of the patient's heart or other three-dimensional geometrical surface (e.g., a sphere). In some examples, the geometry data represents the surfaces of interest as three-dimensional data describing a surface on to which reconstructed signals are computed (by engine 52) and one or more surfaces where invasive measurements are made (e.g., by the IMD electrodes and/or electrodes of an invasive EP monitoring system).

As an example, the geometry data 54 is derived from image data acquired for the patient and includes spatial coordinates for the patient's heart and the electrodes 20 and 36. Image data can be acquired using nearly any imaging modality based on which a corresponding representation can be constructed, such as described herein. Examples of imaging modalities include ultrasound, computed tomography (CT), 3D Rotational angiography (3DRA), magnetic resonance imaging (MRI), x-ray, 3D ultrasound, positron emission tomography (PET), fluoroscopy and the like. Such imaging may be performed concurrently with recording the electrical activity that is utilized to generate the sensed electrical data 40 or the imaging can be performed separately (e.g., before or after the measurement data has been acquired). The location for each of the electrodes 20 and 36 can be provided in the geometry data 54 by acquiring the image while the electrodes are disposed on the patient and identifying the electrode locations in a coordinate system through appropriate image processing, including extraction and segmentation. The resulting segmented image data can be converted into a two-dimensional or three-dimensional graphical representation that includes the volume of interest for the patient. Appropriate anatomical or other landmarks, including locations for the IMD 12, as well as the electrodes 20 and 36, can be identified in the geometry data 38 to facilitate spatial registration of the electrical data 48. The identification of such landmarks can be done manually (e.g., by a person via image editing software) or automatically (e.g., via image processing techniques).

In some examples, the geometry data 38 represent anatomic and electrode geometry as a mathematical model, which can be a generic model or a model that has been constructed based on image data obtained for the patient. Alternatively, or additionally, the geometry data 38 can include a generic or custom representation (e.g., a model) of the heart, which may not be the patient's own heart. In such a case, the sensed electrical data 40 can be mapped (e.g., via registration) to the representation of the organ according to identified anatomical landmarks.

As a further example, the reconstruction engine 52 is programmed to calibrate the heart-torso model to take into account inhomogeneity of the patient's body between the heart and the surface electrode locations. For example, the monitoring system 14 may be programmed to control the IMD 12 to generate a calibration signal (e.g., an electrical signal) by one or more of the IMD electrodes 20. In other examples, the monitoring system 14 can provide instructions to the signal generator 44 to control one or more of the EP electrodes 36 to generate the calibration signal. The reconstruction engine 52 or another method (e.g., signal processor 40) is programmed to determine impedance of a patient's body between the respective IMD electrodes 20 and respective surface electrodes 36 responsive to the calibration signal. For example, variations in the amplitude of signals generated by the IMD electrodes 20 and measured by the body surface electrodes 36 can provide information relative to variations in transthoracic impedance. Frequency of the calibration signals may also be varied as part of determining transthoracic impedance between the respective electrodes 20 and 36. For example, the impedance can be utilized to generate an impedance map of the patient's body. The impedance data thus may be used to calibrate model data that characterizes inhomogeneity of a patient's body between the heart and the surface electrode locations based on the impedance. User interface 60 may be used in some examples to selectively employ the impedance information to calibrate the model data accordingly. For example, inhomogeneities may be selectively applied to the part of a heart-torso model that represents conductivity of the patient's body, such that some of the volume-body conductor may be represented as a homogeneous conductor and other portions of the volume-body conductor represented by the model may reflect inhomogeneities. The reconstruction engine 52 thus may compute reconstructed electrical signals on the surface of interest using the calibrated model data.

In another example, additionally or alternatively to the features described herein, the reconstruction engine 52 further may be programmed to determine one or more boundary conditions based on the IMD data 46 and 58. The boundary condition may be applied automatically or be selectively applied in response to a user input (e.g., through user interface 60). The reconstruction engine 52 further may be programmed to compute reconstructed electrical signals on the surface of interest based on the synchronized electrical data 48, including signals measured by the IMD electrode 20 and the EP electrodes 36, the geometry data 54 in which the reconstruction engine imposes the boundary conditions to restrain the computations being implemented to determine the reconstruction electrical signals.

The monitoring system 14 also includes a map generator 64 that is programmed to generate an EP map that can be rendered on a display 68 to graphically visualize the reconstructed electrical signal on the surface of interest. As disclosed herein, the surface of interest may be an epicardial surface, an endocardial surface, or a combination of an epicardial or endocardial surfaces. Additionally, the surface of interest can be a cardiac envelope, such as a surface residing between the center of a patient's heart and the body surface where the electrodes are positioned. The surface of interest may encompass the entire cardiac surface or one or more surface regions (epicardial or endocardial) such as described herein.

The map generator 64 thus provides output data 66 that may be provided to the display 68 to visualize one or more electrocardiographic maps as well as other electrical information derived from the reconstructed electrical signals. For example, the map generator 64 is programmed to generate an EP map based on the reconstructed signals (generated by reconstruction engine) and invasively measured electrical information (e.g., from the IMD and/or an invasive EP monitoring system). By including reconstructed electrical signals (derived from non-invasive measurements) and actual signals (measured invasively) in a combined EP map, the combined EP map concurrently provides respective global and local assessments in the EP map. Additionally, or alternatively, the reconstructed electrical signal on surface of interest may further be enhanced through electrical signals acquired concurrently by invasive measurements, including by the IMD and/or invasive electroanatomic mapping systems.

In some examples, the calibration pulses can be used in a similar manner to synchronize data acquired invasively by the IMD and an invasive EP monitoring system. The reconstruction engine 52 thus may temporally and spatially combine the synchronized invasive measurements from the IMD and the invasive EP monitoring system into an EP map of corresponding electrical signals based on the respective IMD electrical data, the EP electrical data and corresponding geometry data representing spatially where the invasive measurements are acquired. The map generator 64 is programmed to generate a visualization based on the EP map of the corresponding invasive electrical signals.

As a further example, the monitoring system 14 may include a virtual physiological (EP) study function 70. The virtual EP study function 70 is a set of executable instructions programmed to enable a user to perform an EP study for a patient without requiring a catheter or other probe to be physically inserted within the heart. Instead, the virtual EP study function 70 leverages communications link 16 between an already-implanted IMD 12 and the monitoring system 14 and the known spatial registration (e.g., in the geometry data) and electrical registration (e.g., by synchronization function 50 synchronizing the electrical data 48) to perform the study.

As an example, the virtual EP study function 70 is programmed to control the IMD 12 via the communications link 16 to generate a stimulus signal via one or more of the IMD electrodes 20. For example, after decoding the signal communicated through the link 16, the communications module 18 may provide the processor 30 with decoded instructions from the function 70. The processor 30 executes the instructions and controls the signal generator 26. In response, the signal generator 26 may provide a respective stimulus signal (voltage or current) supplied to one or more of the IMD electrodes 20 (e.g., a single pulse from a single electrode or a potential between a pair of electrodes).

For example, a stimulus may be a suprathreshold signal to stimulate a region of the heart where respective electrodes have been fixed. Because the position of each of the electrodes 20 is known and stored in the IMD geometry data 58, the EP study function 70 can provide different stimulus signals (e.g., having different signal parameters such as amplitude, pulse width and, if needed, frequency). The resulting cardiac signals that propagate across the heart responsive to each such stimulus signals may be recorded as electrical data 48. For example, the cardiac signals responsive to the stimulus signal may be measured invasively by one or more other implanted electrodes 20 as well as by measurements by the EP electrodes 36. Signals measured by IMD electrodes may be stored in memory 28 as IMD data and be communicated to the monitoring system via the link 16, as described herein.

In some examples, the stimulus signal may be utilized by the synchronization function 50 (as a synchronization signal) to synchronize the signals during the virtual EP studies that are being implemented. The measured electrical activity may be stored in memory as electrical data 48, including both IMD data 46 and EP data 42 responsive to the stimulus signal that is generated. The virtual EP study function 70 then may employ the reconstruction engine 52 to compute reconstructed electrical signals on the surface of interest based on the measured electrical activity (e.g., synchronized electrical data 48) and the geometry data 58, as described herein.

As a further example, the stimulus signals may be used to refine the models and/or to assess the electrical characteristics of certain regions, which may be the same or different region from where stimulus signals are applied. For example, pacing from multiple locations and with varying rates and frequencies (e.g., extrasystolic beats) can help to define the electrical properties of local tissues, such as including conduction velocities, refractory periods, and the like. Electrical signals reconstructed across the surface of interest, including multiple chambers or the entire heart, which are reconstructed (by reconstruction engine 52) responsive to the stimulus signals, further may provide a global assessment of the stimulus on cardiac tissue. For example, the global assessment may show effects of such stimulus at one or more regions that are different from where the stimulus signals are applied or across the entire surface of the heart.

In some examples, where additional IMD electrodes 20 and/or other invasive electrodes are positioned to measure the cardiac response to the stimulus signal, the surface of interest may include both an endocardial surface as well as an epicardial surface. The map generator 64 may in turn generate electrocardiographic map that is provided as output data 66 and rendered on the display 68. Additionally, in some examples, the virtual EP study may use a user interface 60 to enable a user to trigger application of the stimulus signal through the communications link 16 in response to a user input made with the user device 62. In one example, the user device may include a trigger or button in a form factor and configuration similar to the trigger or the stimulus control that is provided for an EP catheter.

By way of further example, the stimulus signal may be used to generate a series of cardiac maps (based on reconstructed electrical signals on the surface of interest during a series of stimulus signals) that are evaluated to determine control parameters, such as pacing parameters for use by the IMD to perform pacing (e.g., cardiac resynchronization therapy (CRT)) or another forms of cardiac rhythm therapy (e.g., cardioversion and/or defibrillation). For example, the study function 70 may control the IMD 12 via the link 16 to provide a series of different stimulus signals from selected electrodes 20 and/or having different stimulation parameters. Examples of some stimulus signals that may be used for ventricular pacing stimulus and sensing, which may vary depending on the location and type of electrodes, are shown in the following table. In the example table, the IMD includes left ventricular electrodes LVi (where i is an electrode identifier specifying respective electrode), a right ventricular ring electrode (RV Ring) and a right ventricular tip electrode (RV Tip). Other numbers and types of electrodes may be used in any combination, which may be controlled by the EP study function 70 to provide various stimulus signals and to sense cardiac electrical activity endocardially.

| |
|---|
| RV Tip to RV Ring |
| LV1 to RV Coil |
| LV1 to LV2 |
| LV1 to LV3 |
| LV1 to LV4 |
| LV2 to RV Coil |
| LV2 to LV1 |
| LV2 to LV3 |
| LV2 to LV4 |
| LV3 to RV Coil |
| LV3 to LV1 |
| LV3 to LV2 |
| LV3 to LV4 |
| LV4 to RV Coil |
| LV4 to LV1 |
| LV4 to LV2 |
| LV4 to LV3 |

In some examples, the reconstruction engine 52 may be configured, in response to the user input via the user interface 60, to reconstruct the electrical activity on the surface of interest based on the EP electrical data 42 but in the absence of using the IMD data 46. Then, in response to a further user input via the interface 60 or as part of an automated workflow, the reconstruction engine 52 may reconstruct electrical activity on the surface of interest utilizing the same BSE electrical data 42 and synchronized IMD data 46 so that the input cardiac information from the IMD 12 can augment and correct deficiencies. A user may use both maps to identify differences based on the additional intracardiac measurements or the maps may be combined into a comparative graphical map that is provided as output data 66 to the display 68. In some examples, weighting and scaling of cardiac signals can be applied to increase the contribution of the intracardiac measurement with respect to reconstructed electrical activity generated from body surface electrical measurements. Additionally, the intracardiac measurements by one or more electrodes 20 may be registered (spatially and temporally) with the reconstructed electrical data to provide additional information both epicardially and endocardially, for example.

Figure 2:
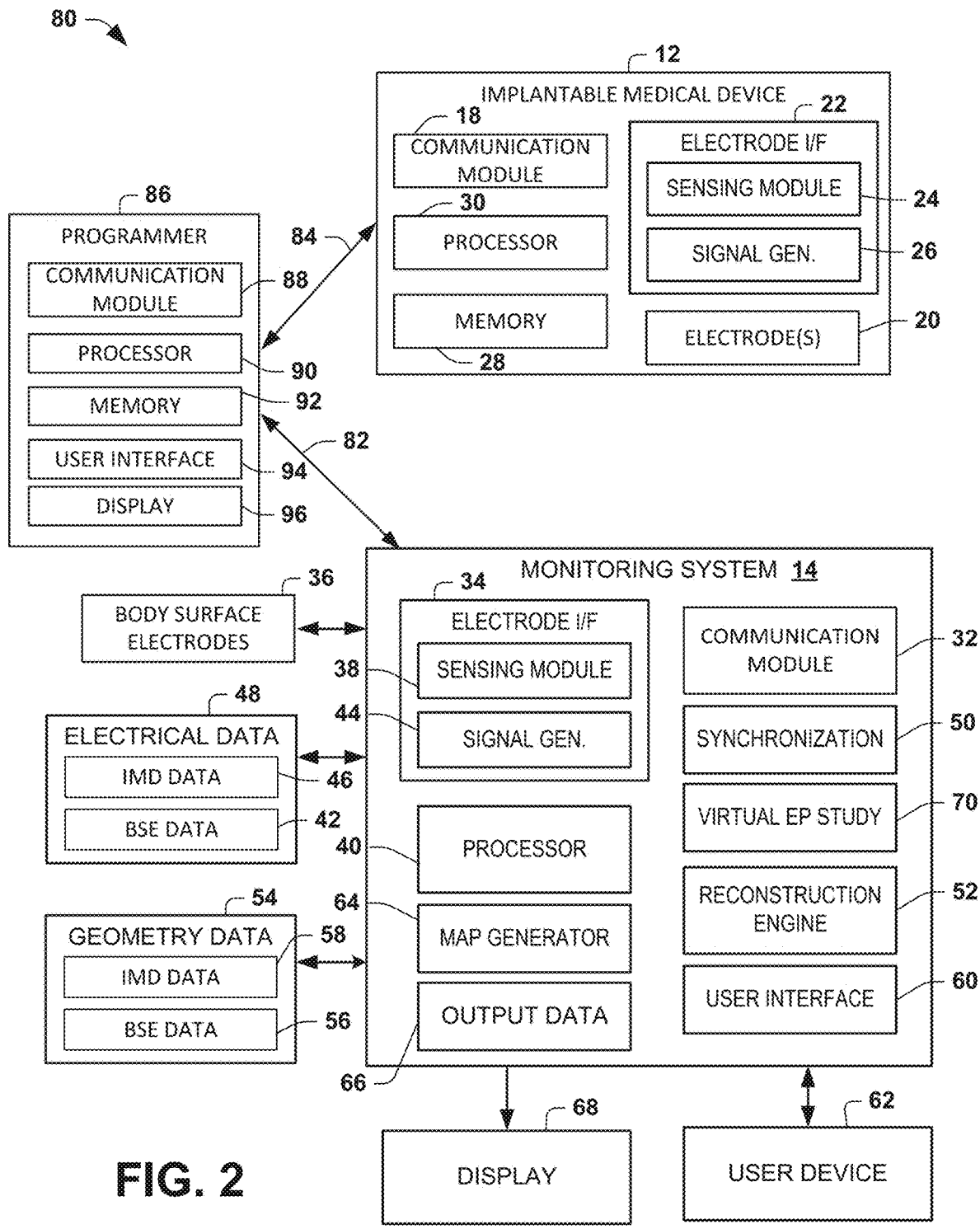
FIG. 2 depicts an example of another system that includes an implantable medical device, programmer and electrophysiology monitoring system.

FIG. 2 depicts another example system that includes an IMD 12 to augment a noninvasive cardiac monitoring system 14. The system 80 in FIG. 2 is identical to the system of FIG. 1. The same reference numbers are used in FIG. 2 to refer to features and components described herein with respect to FIG. 1 and new reference numbers refer to features introduced in FIG. 2. In FIG. 2, the communications link 16 includes multiple link portions, shown as a first link 82 and a second link 84. The first link 82 is a communication link between the monitoring system 14 and a programmer 86. The second link 84 is between the programmer 86 and the IMD 12.

The communications between the IMD 12 and the monitoring system 14 pass through the programmer 86. In one example, the programmer may operate in a passive manner and receive a signal via one of the links 82, 84, decode and re-encode the signal and send it out over the other link. In another example, the programmer may operate more actively by analyzing (or interpreting) the decoded data. The programmer may generate its own instructions and data based on the decoded data received via a link 82, 84 and/or re-package the data in a new container that is formatted (e.g., according to a predefined schema) for the recipient (the IMD 12 or system 14).

The programmer 86 includes a communications module 88 configured to communicate with the communications module 32 through bi-directional link 82 and to communicate with the IMD communications module 18 through bidirectional link 84. The programmer also includes a processor 90, memory 92, a user interface 94 and a display 96. For example, the communications module 88 may include multiple communications interfaces, including at least one for communication with the IMD 12 and another for communication with the monitoring system 14. The physical layer implementation for each interface depends on the physical layer implemented by each link 82 and 84.

In an example, the communication link 84 between the programmer 86 and IMD 12 is a wireless link (e.g., Bluetooth, WiFi, cellular data or the like). The communication link 82 between the monitoring system 14 and the programmer 86 may be a wireless link or a physical link (e.g., electrically conductive wires or optical fiber) or it may include more than one type of physical layer.

As a further example, the communications module 32 is configured to communicate with the programmer 86 via the link 82. The communications module 18 of the IMD 12 is likewise configured to communicate with the programmer 86 through the link 84. Thus, the communications module 88 may include multiple communication interfaces, such as a wireless interface to communicate over the link 84 and another interface to communicate over link 82 with the communications module 32.

In some examples, programmer 86 may be a handheld device or a microprocessor-based home monitor or bedside programming device. A user, such as a physician, technician, nurse or other clinician, may interact with programmer 86 to communicate with IMD 12. For example, the user may interact with programmer 86 via user interface 94 to retrieve currently programmed operating parameters, current physiological data and/or historical physiological data collected by IMD 12, or device-related diagnostic information from IMD 12. A user may interact with programmer 86 to program IMD 12, e.g., select values for operating parameters of the IMD.

A user may also interact with the programmer to establish the communication link 82 with the monitoring system 14 and to enable the monitoring system 14 to implement control and programming of the IMD. When the monitoring system is connected with the programmer 86 via the link 82, a user may employ the user interface 60 to take over operation of the programmer 86 for controlling operation of and/or programming the IMD 12. For example, a user interacting with the monitoring system 14 via user interface 60 can initiate the virtual EP function 70 to perform an EP study, as described herein. A user can also perform other functions via the user interface 60, such as including a CRT optimization procedure performed by IMD 12 automatically or semi-automatically, to establish data for closed-loop optimization of CRT control parameters. The user may evaluate the output data on the display (e.g., electrocardiographic maps) to determine CRT control parameters for programming the IMD 12.

In some examples, programmer 86 may include a programming head (not shown) that is placed proximate to the patient's body near the IMD 12 implant site to enable communications via link 84. In other examples, programmer 86 and IMD 12 may be configured to communicate using a distance telemetry algorithm and circuitry that does not require the use of a programming head and does not require user intervention to maintain a communication link.

In some examples, the link 82 may be a communications network (e.g., local area network) to which the communications module 88 is coupled for communicating data to and from the monitoring system 14. Additionally, a remote user further may access the programmer 86 and/or the monitoring system 14 via the network link from a remote computer or workstation to allow remote monitoring and management of IMD 12 and the monitoring system 14.

Additionally, the monitoring system 14 may retrieve historical data that has been stored in the memory 92 of the programmer based on electrical signals measured by the IMD 12 and provided to the programmer via the link 84. For example, electrical signal measurements may be made by one or more electrodes of the IMD 12 over multiple measurement intervals over an extended period of time (e.g., days or weeks), and the electrical data may be stored in the memory 92. The monitoring system 14 may retrieve the data for displaying the measured signals and be configured to perform further analysis, which may include automatic analysis by the signal processing function and/or analysis by a user based on a visualization of the stored signals on a display.

By way of example, the IMD 12 may be programmed to store historical electrical data based on measured cardiac signals acquired by one or more implanted leads 20 to represent electrical activity associated with a known cardiac event. The implanted leads of the IMD 12 may include endocardial leads, epicardial leads or a combination of endocardial and epicardial leads. The locations of each lead and its respective electrode(s) 20 are at known locations in the heart. The electrical measurement data for one or more cardiac events (e.g., one or more cardiac intervals) may be stored in memory of the IMD 12 responsive to detecting a respective cardiac event. Examples of recurring cardiac events, which may be stored in the memory 28 of the IMD 12, include premature ventricular contraction (PVC), acute coronary syndrome (ACS) and congenital long QT syndrome to name a few.

The reconstruction engine 52 of the monitoring system 14 thus can reconstruct electrical activity for a region or the entire heart based on non-invasively measured electrical data, as described herein. The monitoring system 14 can also receive the electrical measurement data for a respective cardiac event, as measured at one or more known cardiac locations, through the link 82. The monitoring system 14 includes instructions (e.g., program code) further configured to locate a region or points in the reconstructed cardiac data corresponding to the one or more known cardiac locations where the event was measured by the IMD 12. After the regions or points in the reconstructed electrograms are aligned spatially with respective location(s) where the IMD measured the cardiac event (e.g., PVC or other event), the monitoring system 14 is configured to compare the reconstructed electrical signals for another detected instance of the cardiac event with the recorded electrical signals for a prior instance of the event. Alternatively, a template may be created (e.g., by the monitoring system 14 or programmer 86) based on the recorded signal of the prior instance of the cardiac event, and the template is compared with the reconstructed signals for the region or points corresponding to the recorded measurement locations. The comparison (a difference between the reconstructed and recorded signals) can be used by monitoring system 14 to determine an accuracy of the reconstructed electrical signals.

In an example, the monitoring system 14 is configured to adjust the reconstruction method (e.g. inverse solution) based on the comparison so the reconstructed electrical signals better match the signals recorded by the IMD 12 for the event. For example, the adjustment can include adjusting the reconstructed signals spatially to minimize a difference between the reconstructed signals and the signals recorded by the IMD for the event. Alternatively or additionally, the locations of reconstructed signals that correlate more highly with the recorded IMD signals can be weighted more heavily in a transfer function used for solving the inverse solution to reconstruct the electrical signals.

In a further example, activation time of cardiac signals at one or more known locations may be determined based on cardiac signals measured by one ore electrodes 20 of respective the implanted leads of the IMD 12. The monitoring system may use the activation time derived from the directly measured signals to improve a corresponding activation map generated by the monitoring system based on reconstructed cardiac signals (generated from non-invasively measured cardiac signals). For example, the monitoring system 14 is configured to compute a difference between the activation time for electrodes 20 of the IMD 12 and the activation time for a set of cardiac nodes (nodes localized at or near the IMD electrode locations) for which the electrical signals have been reconstructed. The monitoring system 14 can use the computed difference between respective activation times to augment (e.g., optimize) the activation map. In one example the activation map augmentation includes the monitoring system 14 assigning a greater weight to nodes that are temporally and spatially synchronized (i.e., consistent) with respect to the IMD electrodes 20 for which activation time has been determined. In another example, the activation time determined for electrodes 20 of the IMD 12 may be used as a boundary condition that is used by the reconstruction engine 52 for computing reconstructed electrical signals on the cardiac surface of interest (e.g., a region or the entire heart). In yet another example, the monitoring system 14 is configure to minimize (e.g., by implementing a least squares or other minimization algorithm) the difference between the activation time the IMD electrodes 20 and the activation time for reconstructed cardiac signals.

As a further example, monitoring system 14 is configured to identify previous arrhythmogenic activity (an event) on or in the patient's heart based on historical data recorded by the IMD 12. The identified activity or event may be used as a starting point for further analysis by the monitoring system 14 based on reconstructed electrical activity on a cardiac envelope based on non-invasively acquired electrical measurements. For example, the monitoring system 14 may be configured to record electrical data (EP data 42 and/or IMD data 46) and reconstruct electrical signals on a surface of interest that includes a region of interest where the arrhythmogenic activity was identified in response to cardiac electrical signals measured by the IMD electrodes 20. Additionally, or alternatively, the virtual EP study function 70 may provide instructions to the IMD to deliver one or more stimulus signals to the region where the arrhythmogenic activity was identified or other regions to observe local and/or global electrical activity for the heart as demonstrated in reconstructed electrical signals.

Figure 3:
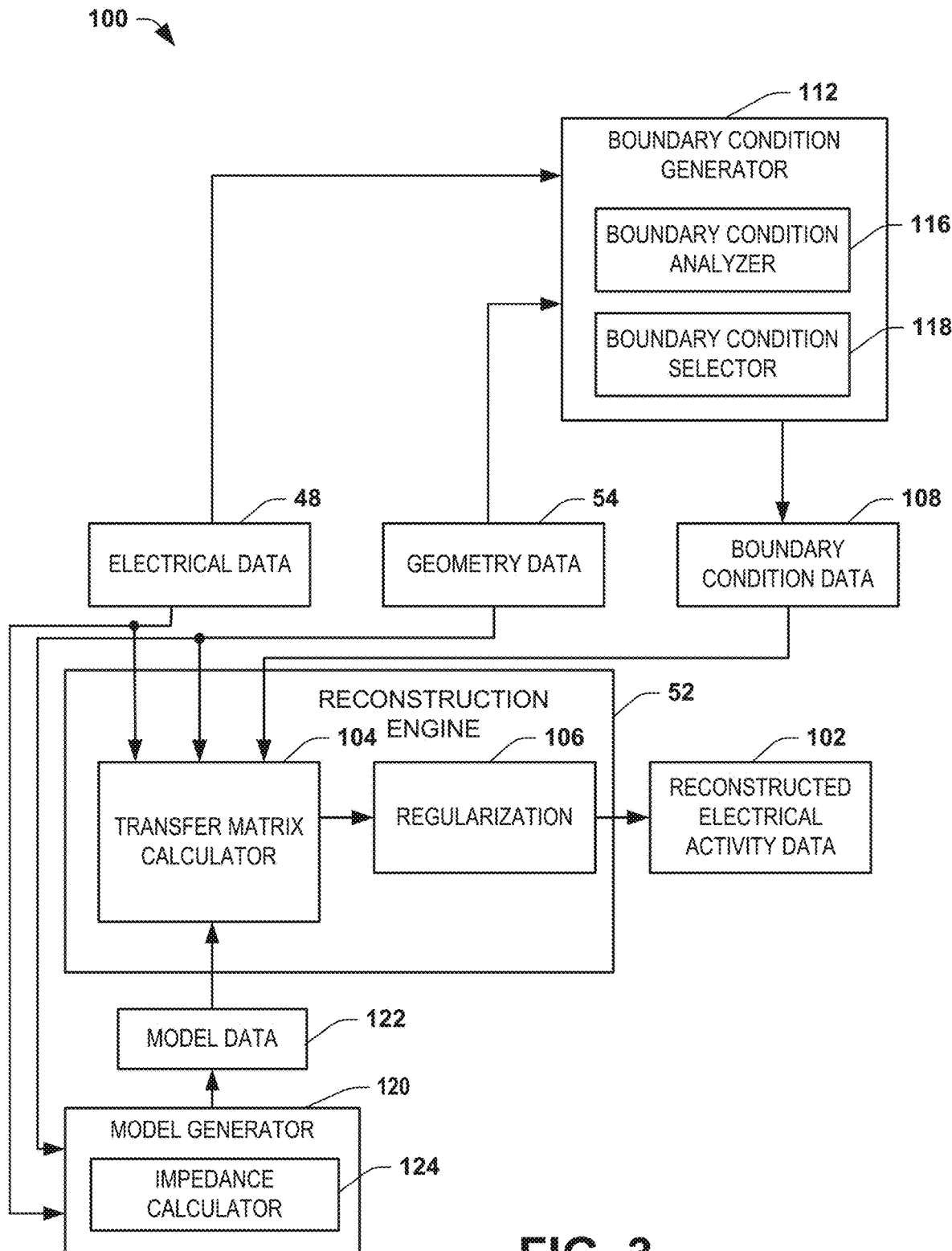
FIG. 3 depicts an example of a reconstruction engine.

FIG. 3 depicts an example system 100 that includes a reconstruction engine to reconstruct electrical signals on a surface of interest, such as described in example systems 10 and 80 of FIGS. 1 and 2. The example system 100 is described in the context of the reconstruction engine 52 being programmed to employ a boundary element method as part of the inverse solution. It will be understood that the reconstruction engine can be programmed to utilize other techniques for solving the inverse problem. As one alternative example, the reconstruction engine 52 may be programmed to implement a meshless approach that uses the method of fundamental solution such as disclosed in the above-incorporated U.S. Pat. No. 7,983,743.

The system 100 includes a reconstruction engine 52, which may be used as the reconstruction engine in of FIGS. 1 and 2. The reconstruction engine 52 can generate reconstructed electrical activity data 102 by combining measured electrical data 48 and geometry data 54 and. In the example of FIG. 3, the reconstruction engine 52 is programmed to implement an inverse method that is includes a transfer matrix calculator 104 and regularization function 106.

The reconstruction engine 52 further is configured to impose boundary condition data 108 on the computations implemented by the transfer matrix calculator 104. The values defined for each unit of the boundary condition being imposed by the transfer matrix calculator 104 can include fixed or variable boundary condition parameters.

In some examples, the system 100 includes a boundary condition generator 112 to generate the boundary condition data 108. The boundary condition generator 112 includes a boundary condition analyzer 116 and a boundary condition selector 118. The boundary condition analyzer 116 is programmed configured to analyze supplemental information, such as IMD information stored as part of the electrical data 48 and the geometry data 54. For example, the analyzer 116 can evaluate each unit of data to ascertain whether it represents a valid boundary condition (e.g., to determine the efficacy of the supplemental information as a boundary condition for the inverse method). The validity of a boundary condition can depend on the supplemental information, such as including its value and/or associated location. The boundary condition selector 118 can be configured to select boundary conditions determined by the analyzer 116 to be valid. Additionally, the boundary condition selector 118 can be configured to exclude the supplemental information if the analyzing indicates that the supplemental information provides an invalid boundary condition for the inverse method. In some examples, the boundary condition selector 118 is programmed to select which one or more IMD electrodes will be used as boundary condition data 108 in response to a user input (e.g., via user interface 60).

As an example, the geometry data 54 further may include information describing cardiac electrophysiology, which can include fiber angles and orientation of myocardial fibers between the endocardium and epicardium. The reconstruction engine 52 thus can be configured to estimate a conduction orientation for reconstructed signals on a cardiac envelope (e.g., epicardial surface) based on the based on the fiber angles and thickness of the cardiac tissue between respective endocardial and epicardial surfaces. Alternatively, the fiber angles may be determined separately and stored with the geometry data 54. The reconstruction engine 52 can also determine conduction velocities and delays based on comparing temporally aligned recorded measurements by the IMD electrodes 20 and reconstructed cardiac signals based on non-invasive measurements. For example, if the IMD electrodes 20 are on the endocardium and the ECGI reconstruction is on the epicardium, the reconstruction engine 52 can estimate electrical conduction velocities and cardiac fiber angles between endocardial and epicardial surfaces that would result in a conduction delay, enabling the determination of a correction factor—at least for regions localized in proximity of the known locations of the IMD electrodes. The reconstruction engine 52 thus can employ the correction factor (e.g., as well as fiber angle and thickness) for respective locations on the epicardium to translate or map respective reconstructed epicardial signals from the epicardium to corresponding endocardial locations. That is, the reconstruction engine 52 is configured to translate reconstructed ECGI map data to an endocardial surface based on the fiber angle and conduction orientation. A corresponding endocardial map for a surface (or surfaces) of interest may then be generated (e.g., by map generator 64) from portions of endocardial map that have been translated onto the endocardial surface by applying the correction factor and rendered on a display.

As a further example, the electrical activity measured by one or more IMD electrodes (e.g., IMD electrical data 46) and information representing the three-dimensional spatial location of the respective IMD electrodes (e.g., IMD geometry data 58) may be used to provide boundary condition data 108. As described herein, for example, the IMD includes one or more IMD electrodes (e.g., ring electrodes, plates, or coils) that are attached within the patient's body at fixed locations, which may be known locations or locations that can be determined by a localization system. For example, the electrode locations may be determined as spatial coordinates in 3D space. In some examples, the IMD electrode locations are determined from 3D imaging modality that is used to image patient's body as part of a process to provide geometry for body surface electrodes (e.g., noninvasive EP electrodes 36) as described herein. The IMD data, which is used as boundary condition data 108, thus can represent endocardial and/or epicardial measurements of electrical signals (e.g., potentials) at respective known locations, including direct measurements acquired over time within the patient's body.

In some examples, the IMD data includes electrical signal measurements recorded over a long period of time and stored in memory (e.g., memory of the IMD and/or programmer). The IMD data thus may be retrieved by the monitoring system 14 via the communication link for use by the reconstruction engine 52, as disclosed herein. In other examples, the IMD data that is used for the boundary condition data 108 includes IMD electrical signal measurements acquired by the IMD during an EP study (e.g., in response to instructions from virtual EP study function 70). Because the relative position of the IMD electrodes and body surface electrodes may be determined with high accuracy (e.g., from a common 3D image set), using IMD data as boundary conditions can improve accuracy of the reconstructed signals that are derived from noninvasive EP electrical measurements.

For the example where the transfer matrix calculator 104 is programmed to use BEM (boundary element method), the calculator 104 may employ the boundary condition data 108 to produce an extended linear system that is constrained by each one or more boundary conditions that is applied. For example, the IMD electrical data 46 and/or IMD geometry data 58 may be used to provide one or more intracardiac boundary conditions that are stored in the boundary condition data 108. The electrical data may be obtained from one or more IMD electrodes, as described herein, and thus may be a single measurement or a series of measurements that change over time. The transfer matrix calculator 104 can be programmed to compute an extended linear system in which the boundary condition data 108 has been imposed, such as the following:

$$\begin{bmatrix} A \\ e_{i_1} \\ \vdots \\ e_{i_K} \end{bmatrix} \begin{bmatrix} v_{E_1} \\ \vdots \\ v_{E_N} \end{bmatrix} = \begin{bmatrix} \phi_{B_1} \\ \vdots \\ \phi_{B_M} \\ u_{E_{i_1}} \\ \vdots \\ u_{e_{i_K}} \end{bmatrix} \quad Eq.\ 1$$

where:
matrix A is of size M×N generated by BEM approach,
$V_{Ei}$ represents the unknowns of potentials at heart surface,
$\phi_{Bi}$ represents measured body surface potentials,
$e_{i_k}$ represents unit 1×N vector with $e(i_k)=1$, and
$u_{E_{ij}}$ represents IMD electrical data (e.g., data 46 in FIGS. 1 and 2)
measured from the heart surface.

As an additional or alternative example, where a scar/lesion based of an boundary condition is also included in the boundary condition data 108, such as may be stored in the IMD geometry data 58 (e.g., derived from image data), the transfer matrix calculator 104 can be programmed to compute an extended linear system in which each such boundary condition data has been imposed, such as the following formulation:

$$\begin{bmatrix} A \\ e_{i_1} \\ \vdots \\ e_{i_K} \end{bmatrix} \begin{bmatrix} v_{E_1} \\ \vdots \\ v_{E_N} \end{bmatrix} = \begin{bmatrix} \phi_{B_1} \\ \vdots \\ \phi_{B_M} \\ 0 \\ \vdots \\ 0 \end{bmatrix} \quad Eq.\ 2$$

While in the example of Eq. 2, the boundary condition sets the voltage potential at the known locations defined by the boundary condition to zero (e.g., 0 V), as mentioned other fixed low voltage values could be used in other examples. In still other examples, the boundary conditions for locations corresponding to the identified scar/lesion region in Eq. 2 and/or the measured intracardiac locations of Eq. 1 may be expressed in bipolar measurement format, such as corresponding to measurements between respective pairs of IMD electrodes 20. In such bipolar examples, the above Eqs. 1 and 2 would be modified to replace the extended vector according to the following bipolar expression:

$$\mu(x_{si}) - \mu(x_{sj}) = 0 x_{si}, x_{sj} \in S \subset \Omega \text{scar/lesion} \quad Eq.\ 3$$

Additionally, the systems and methods disclosed herein can assign different weights on the scar/lesion prior to adjust its impact spatially on the system, based on a certainty of this kind of prior supplemental information. For example, scar, lesion or other conduction defects can be defined using methods described herein with respect to virtual EP study function 70 or through local measurements of impedance.

The regularization function 106 is programmed to apply a regularization technique to solve the unknown values of electrical activity on the envelope of interest (e.g., $V_{Ei}$ in Eqs. 1 and 2) from the transfer matrix computed by the calculator 104. As an example, the regularization function 106 is programmed to implement Tikhonov regularization, such as described U.S. Pat. No. 6,772,004. In another example, the regularization function is programmed to employ another regularization technique, such as generalized minimum residual (GMRes) regularization, such as disclosed in U.S. Pat. No. 7,016,719, which is incorporated herein by reference. Other regularization techniques (e.g., Singular Value Decomposition (SVD) or Truncated Singular Value Decomposition (TSVD), can also be applied, in addition to, or in lieu of, the techniques mentioned above. The reconstruction engine 52 can in turn provide the reconstructed electrical activity based on the regularized matrix.

In an additional or alternative example, the system 100 (part of monitoring system 14) may include a model generator 120 programmed to generate model data 122 representing three-dimensional transthoracic impedance (e.g., conductivity) of a patient's body between the patient's heart and body surface (e.g., where body surface electrodes are positioned). For example, the model generator 120 includes an impedance calculator 124, which is implemented as instructions executed by a computer processor in the system 100, programmed to calculate impedance of the transthoracic cavity (throughout the body conductive volume) based on the electrical data 48 representing electrical signal measurements between one or more of the IMD electrodes 20 and body surface electrodes (e.g., electrodes distributed across the patient thorax). For example, the monitoring system 14 is configured to control respective signal generators 26 and 44 to apply fields (e.g., inject electrical energy in the form of current or voltage) between respective pairs of the electrodes 20, 36. The electrode pairs may be pairs of IMD electrodes, pairs of body surface electrodes or pairs that include one IMD electrode and one body surface electrode.

For example, volumetric impedance data further may be estimated and used to model inhomogeneities of the transthoracic cavity that is implemented in a torso model used by the reconstruction engine 52 for solving the inverse problem when reconstructing signals as described herein. For example, the volumetric impedance data may be estimated from imaging data and/or based on one or more transthoracic impedance measurements (e.g., measured between an invasive electrode and one or more body surface electrodes). In an example, the impedance data may include an intrathoracic impedance information as measured by between IMD electrodes (e.g., between one or more leads within the heart and an ICD in the chest), such as based on thoracic fluid monitoring (e.g., by Optivol fluid status monitoring, available from Medtronic, Inc. of Minneapolis, Minn.).

In one example, the monitoring system controls one or more signal generators to apply a potential (or electrical current) between one or more pairs of electrodes, namely one IMD electrode and one or more body surface electrodes. A response is measured at other electrodes as the applied potential is delivered between the respective electrode pair. For example, the currents used are relatively small, below the threshold at which they would cause functional stimulation (e.g., a few milli-Amperes of alternating current at a frequency of about 10-100 kHz). Similar measurements can be made for current applied to each electrode pair.

The sensing modules 24, 38 are used to measure voltage responses across respective electrode pairs and to record corresponding measured electrical signals that are stored in the EP data 42. The impedance calculator 124 thus can compute an indication of impedance between respective electrode pairs throughout the volume. The model generator 120 can determine the conductivity of the transthoracic cavity based on the determined impedance and associated geometry data 54. In an example, the model generator 120 uses the determined impedance data between electrode pairs and geometry data to provide a three-dimensional representation of impedance characteristics for the transthoracic volume of the patient (e.g., a voxelized impedance map).

As a further example, impedance calculator 124 may utilize an Equivalent Single Dipole (ESD) method to determine impedance of the body volume. ESD is an approach that can be employed to represent a potential φ generated by a single dipole in an infinite homogeneous medium. The potential φ can be defined as follows:

$$\phi(x, r', p) = \frac{1}{4\pi g} \frac{p \cdot (x - r')}{|x - r'|^3} \quad (1)$$

where g is the impedance, p is the dipole moment, r' is the dipole location, and x is the location of observation point.

For the example of a system (e.g., system 100) that includes both navigation and body surface mapping, as a user paces from a pair of bipolar catheter leads inside body, a dipole is formed, with the location of the dipole moment p and the dipole location r' given or retrieved from the system. Then for each of the observation point, based on equation (1), the reconstructions engine is programmed to calculate an ideal potential at the observation point x, assuming impedance g is a constant across all directions, comparing with the actual potential measured at the same point, then we can derive a ratio of impedance.

For each one or more pacing sites with measurements across different locations, the same process can be applied to determine the relative ratio of impedance along different directions surrounding the pacing location. This process creates a spherical impedance correction matrix for that pacing site. The same process above can then be applied to multiple pacing sites covering regions of interest around the heart, with different spherical impedance correction matrices calculated at each of the pacing sites.

For an example of an electrical dipole and boundary condition, given the electrical dipole resides spatially within a closed surface T, with dipole location r' and dipole moment p, then the electrical potential measurements p(x) at spot X (e.g., electrode locations on the body surface) satisfies the following potential for the closed surface T:

$$\phi_T(x, r', p) = \frac{1}{4\pi} \oint_{\partial T} \phi_T(s) \frac{\partial \left(\frac{1}{r}\right)}{\partial \vec{n}} \cdot ds + \frac{1}{4\pi g} \frac{p \cdot (x - r')}{|x - r'|^3} \quad (2)$$

For a system with both navigation and body surface mapping, as one paces from a pair of bipolar catheter leads inside body, the dipole is formed, with the location of the dipole moment p and the dipole location r' given or retrieved from the system. Then for each of the observation point on body surface, based on equation (2), one can calculate the ideal potential at the observation point x assuming impedance g is a constant across all directions, comparing with the actual potential measured at the same point, then we can derive a ratio of impedance.

For each of pacing sites with measurements on body surface across different locations, the same process can be applied to get the relative ratio of impedance along different directions surrounding the pacing location. This creates a spherical impedance correction matrix for that pacing site. The same process above can then be applied to multiple pacing sites covering regions of interest around the heart, with different spherical impedance correction matrices calculated at each of the pacing sites. Fitting and interpolation of spherical impedance correction matrices can be done, to correct regions that were not paced but are to be mapped.

In some examples, the body is modeled as a uniform (homogeneous) isotropic volume conductor between the cardiac envelope and the body surface (e.g., like that used in a torso-tank experiment). In other examples, the body is modeled as a non-uniform (inhomogeneous) anisotropic volume conductor between the cardiac envelope and the locations on the body surface where the electrodes are positioned. The model generator 120 thus may utilize the volumetric impedance data in the model data 122 to provide a more accurate representation of the intracavity impedance variations (e.g., inhomogeneities) associated with the corresponding anatomical structure of the patient. In this way, because the heart is surrounded by the lungs, fat, bone and muscle tissue, each of which has its own specific conductivity, the torso model and transfer matrix can account for such inhomogeneities based on impedance information (determined by impedance calculator 124).

As an example, the model generator 120 is further programmed to calibrate the model data 122 to reflect the volumetric impedance data, namely, to represent impedance inhomogeneities within the transfer matrix, such as described herein. For example, the model generator 120 is programmed to determine an indication of homogeneity (or inhomogeneity) as a value within the conductive volume between respective pairs of the electrodes. Additionally, or alternatively, the impedance inhomogeneity of the conductive media between any pair of electrodes can be determined in part from imaging data, such as CT or MRI images (e.g., represented as part of the geometry data 54). The inhomogeneity (or homogeneity) thus may can be determined model generator based on imaging data, signal measurements or a combination of imaging data and signal measurements. The model generator 120 thus may utilize the resulting indication of inhomogeneity and impedance data for the conductive volume to calibrate (or generate) the model data, such as to represent the conductivity of the volume conductor between the IMD electrodes and the body surface electrodes.

The transfer matrix calculator 104 may be programmed to compute a transfer matrix based on the electrical data 48, the geometry data 54, boundary condition data 108 and the model data 122. In some examples, the model data is generated based on an estimated homogeneous impedance of the conductive volume. In other examples, the model data is calibrated based on the impedance data determined by the impedance calculator, as described above.

As an example, the following demonstrates the inverse problem for reconstructing electrical signals on a surface of interest with unipolar prior information.

$$\begin{cases} \phi(x) = \phi_T(x) & x \in \Gamma_T, \text{Dirichlet} \\ \dfrac{\partial \phi(x)}{\partial \vec{n}} = 0 & x \in \Gamma_T, \text{Neumann} \\ \phi(y) = \phi_C(y) & y \in \Omega, \text{catheter unipolar} \end{cases}$$

As another example, the following demonstrates the inverse problem for reconstructing electrical signals on a surface of interest based on bipolar prior information $$\begin{cases} \phi(x) = \phi_T(x) & x \in \Gamma_T, \text{Dirichlet} \\ \dfrac{\partial \phi(x)}{\partial \vec{n}} = 0 & x \in \Gamma_T, \text{Neumann} \\ \phi(y_{i,1}) - \phi(y_{i,2}) = \phi_C(y_{i,1}) - \phi_C(y_{i,2}) & \forall\, (y_{i,1}, y_{i,2}) \in \Omega, \\ & \text{catheter bipolar pairs} \end{cases}$$

By way of example, in the Method of Fundamental Solutions (MFS), one can express potentials at each location as follows:

$$\text{where } f(r) = \frac{1}{4g\pi r}$$

With the spherical impedance correction matrix described above, the corrected impedance for each of the (x,y) pairs can be applied, for example, by changing the impedance g from a constant value to be direction dependent value, namely, impedance data determined by the impedance calculator 124.

Figure 4:
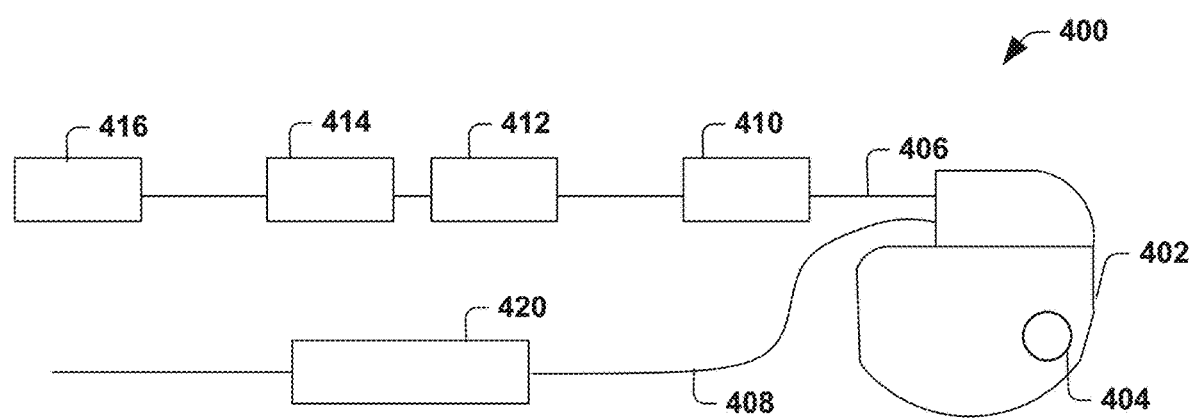
FIG. 4 depicts an example of an implantable medical device that includes one or more leads.

FIG. 4 depicts an example of an IMD 400, which may be used to implement the IMD 12 of FIGS. 1 and 2. The IMD 400 includes a housing 402 that includes the circuitry for performing the functions thereof. For example, the housing 402 includes a communications module processor, memory and an electrical interface. The housing 402 may also include one or more electrodes 404 mounted on the exterior of the housing. The IMD 400 also includes one or more leads 406 and 408 that extend from the housing. There can be any number of one or more leads as part of the IMD 400. The lead 406 includes electrodes 410, 412, 414, and 416 distributed along the length of lead such as for implanting on or in a patient's heart in contacting particular anatomical structures. The lead 408 includes an electrode 420, but in other examples may include more than one electrode. The electrodes 410, 412, 414, 416, 420 may be implemented as ring electrodes, coil electrodes or other shapes of electrodes that may be mounted along the leads.

In one example, the lead 406 may be a left ventricular lead and the lead 408 may be a right ventricular lead. The combination of electrodes further may be used to sense signals that propagate between the anatomic regions in which the electrodes are located. For example, an electrical stimulus signal may be generated by a signal generator implemented in the housing 402 and applied to one or more of the electrodes. The propagation of the signal and response may be sensed by one or more of the other electrodes. For example, the stimulus signal may be delivered by an electrode in one chamber of the patient's heart (e.g., atrium or ventricle) and sensed by an electrode in another chamber of the patient's heart responsive to the stimulus.

Figure 5:
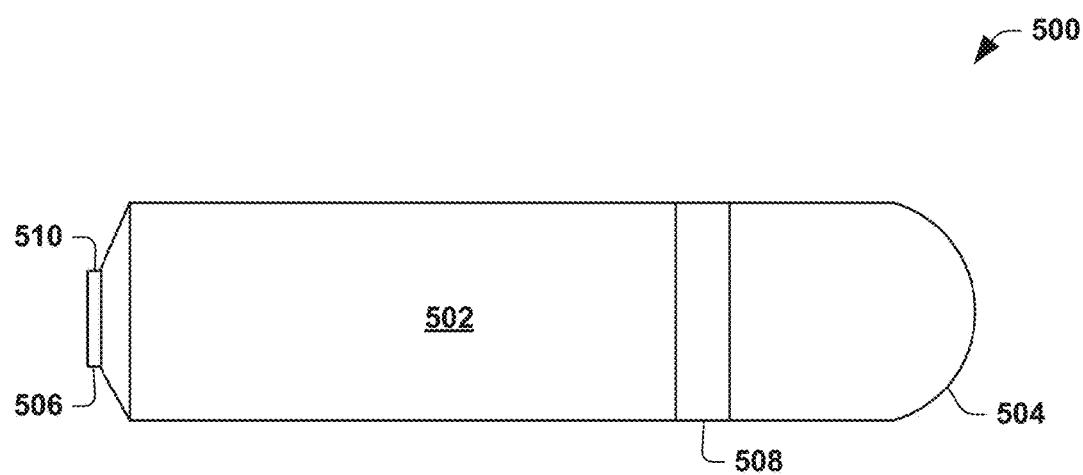
FIG. 5 depicts an example of a leadless implantable medical device.

FIG. 5 depicts another example of an IMD 500 that may be utilized in the systems and methods described herein. The IMD 500 includes an elongated body 502 extending between spaced apart ends 504 and 506. The IMD 500 includes one or more electrodes, demonstrated at 508 and 510 in the example of FIG. 5. The electrode 508 is demonstrated as a cylindrical ring disposed around the body 502 of the IMD 500. There may be any number of one or more such ring electrodes disposed along the body at different locations.

The electrode 510 is an end cap electrode that is disposed at the end 506. The IMD 500 is an example of the leadless IMD. Commercial examples of the leadless IMD include the Micra devices available from Medtronic plc.

Figure 6:
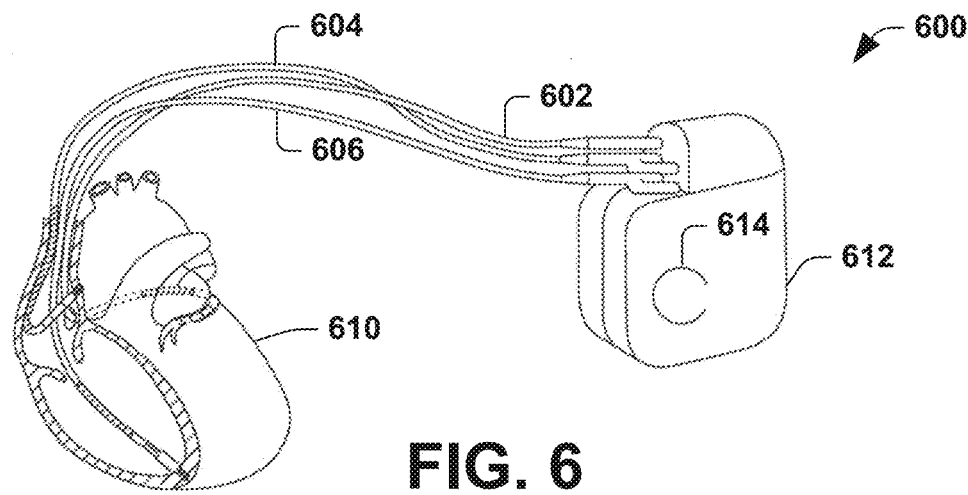
FIG. 6 depicts an example of an implantable medical device having leads implanted in or on a patient's heart.

As a further example, FIG. 6 depicts an example of an IMD 600 in which the plurality of leads 602, 604 and 606 have been fixed within a patient's heart 610. Each of the leads includes one or more electrodes, such as described herein. Additionally, housing 612 of the IMD 600 may include one or more electrodes 614. In the example of FIG. 6, the leads are mounted in the right atrium, right ventricle and left atrium. The leads may be mounted in or on any parts of the heart, including one or more endocardial leads having electrodes for sensing endocardial electrical potentials.

Figure 7:
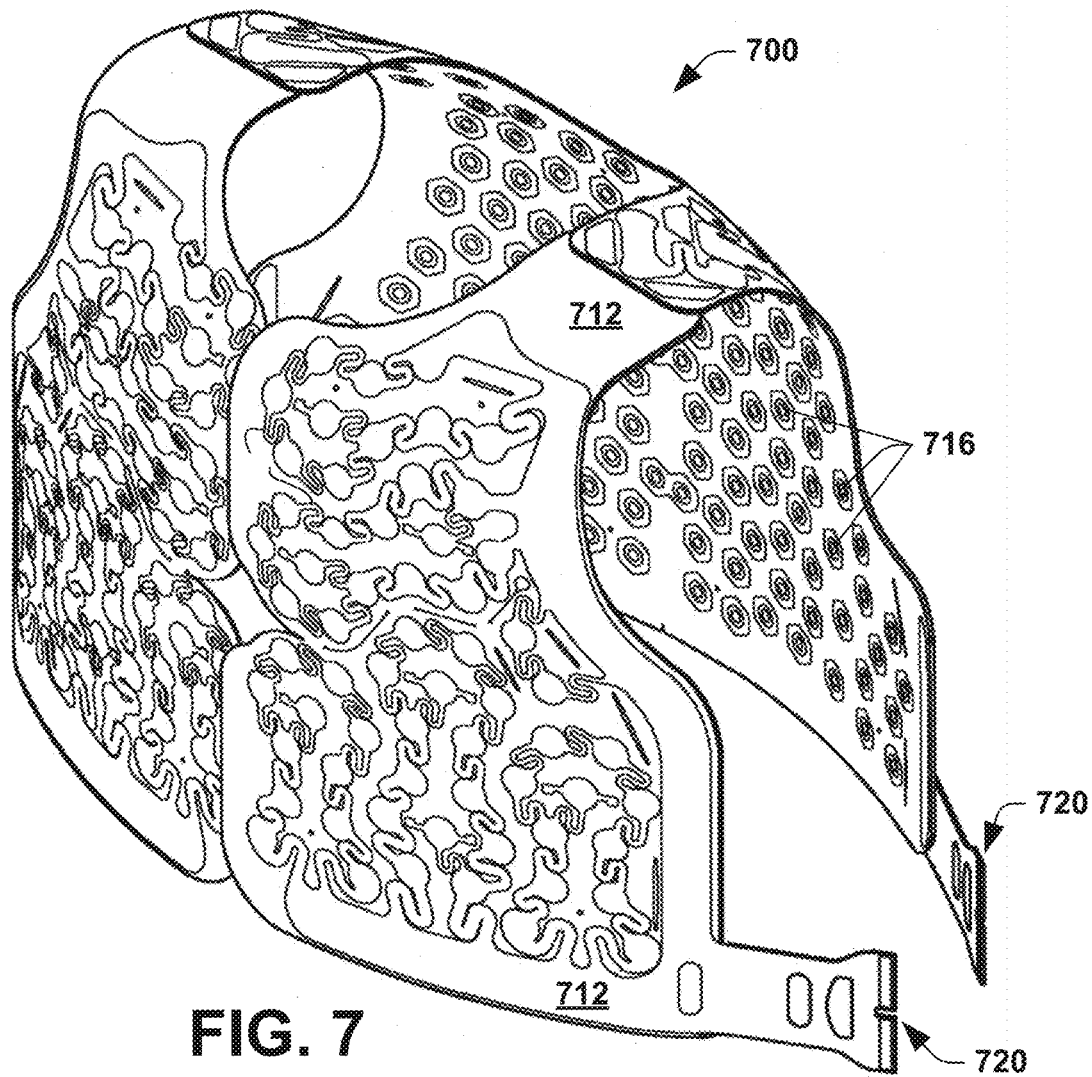
FIG. 7 depicts an example of a sensor array.

FIG. 7 depicts one example of a sensor apparatus 700 that may be attached to a person's torso for noninvasively sensing body surface electrical signals. The example sensor apparatus 700 may be configured according to the embodiments disclosed in U.S. Pat. No. 9,655,561, which is incorporated herein by reference. Other forms and arrangements of electrodes may be used in other examples, such as including the sensor apparatus disclosed in EP Patent No. 2352421.

The example sensor apparatus 10 is dimensioned and configured to be applied to a torso of a patient (e.g., a human patient); however, different configurations can be utilized depending on the patient (e.g., could be human or other animal) and the particular type of electrophysiology to be performed. The sensor apparatus 700 can come in a plurality of sizes to accommodate a range of patient's sizes and body types.

The sensor apparatus 700 may include one or more substrate layers 712 that are formed of a flexible material. The substrate layer 712 provides an electrode-carrying substrate layer. In the example of FIG. 7, the sensor apparatus 700 includes an arrangement of electrodes 716 disposed on a contact surface of a corresponding electrode receiving portion of the substrate layer 712. Respective electrodes 716 can operate as sensors for measuring electrical activity. Additionally, or alternatively, electrodes 716 can be configured to deliver electrical energy (e.g., stimulus signals), as described herein. The electrodes 716 are coupled to a respective connector 720 through electrically conductive element (e.g., a trace or wire). The respective connectors 720 are adapted to couple to an electrode interface (e.g., interface 34), which may be a direct connection or a connection through additional cabling, to carry signal measurements or provide a stimulus signals between the electrode interface and respective electrodes 716.

Figure 8:
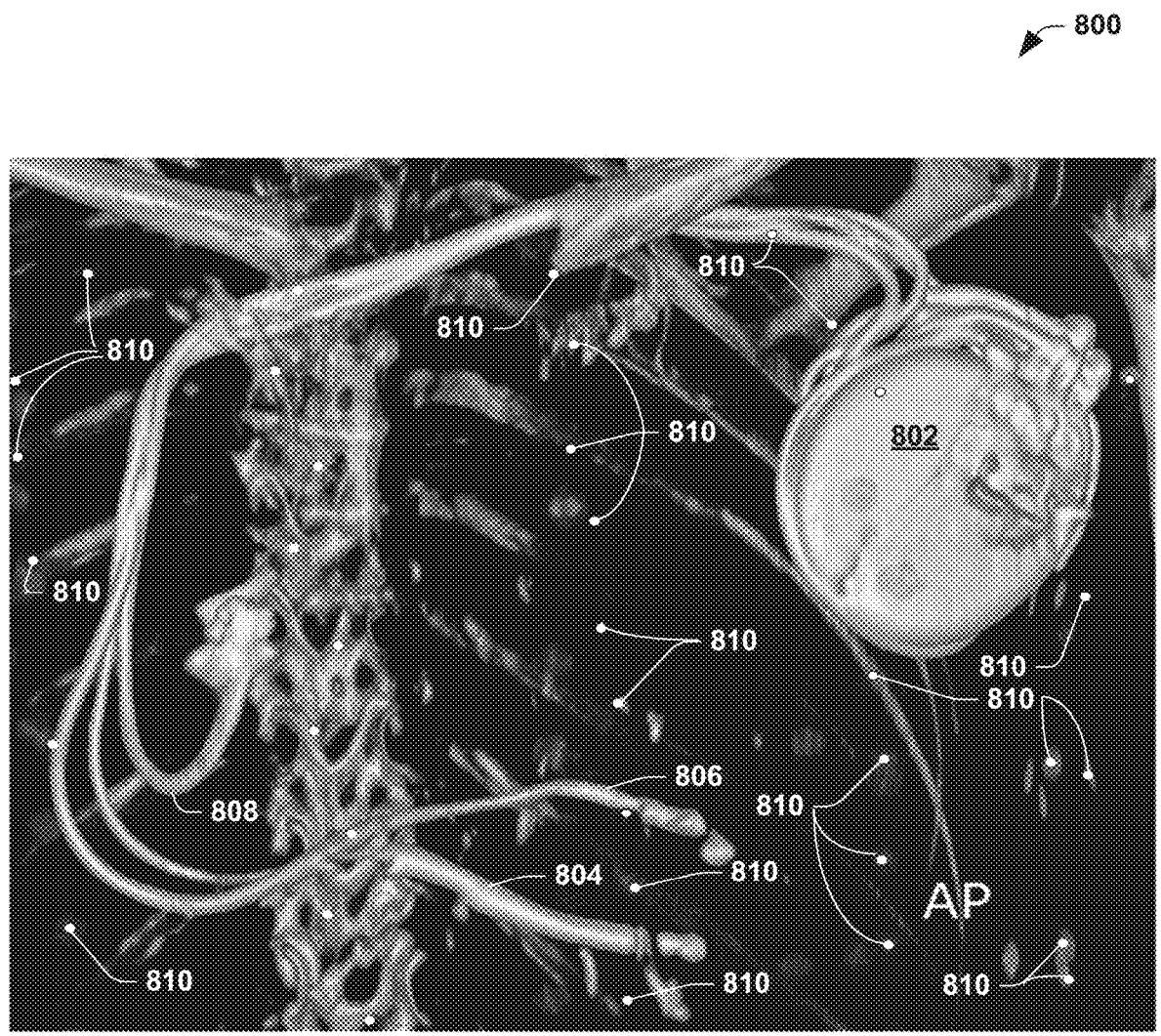
FIG. 8 depicts an example of part of an image that includes an implantable medical device implanted within a patient's body.

By way of further example, FIG. 8 illustrates an image 800 part of a patient's body such as may be acquired by an imaging modality (e.g., x-ray or fluoroscopy). The image 800 includes an IMD 802 implanted within a patient's body. In the example of FIG. 8, the IMD 802 includes leads 804, 806 and 806 extending from the housing of the IMD electronics. In the example of FIG. 8, the IMD 802 includes three leads 804, 806 and 806 that are fixed in the patient's body with respect to the patient's heart. Each of the leads 804, 806 and 806 includes one or more electrodes for sensing electrical signals and/or delivering respective stimulus signals to the heart. The leads 804, 806 and 806 may include respective electrodes in contact with the heart tissue or may be implemented as non-contact electrodes that deliver stimulus or sense signals accordingly.

Also shown in FIG. 8 are body surface electrode locations 810 distributed across the image 800. The electrode locations 810 may be rendered visible in the imaging modality through the use of radio opaque markers or otherwise using radio opaque materials to form the body surface electrodes.

Figure 9:
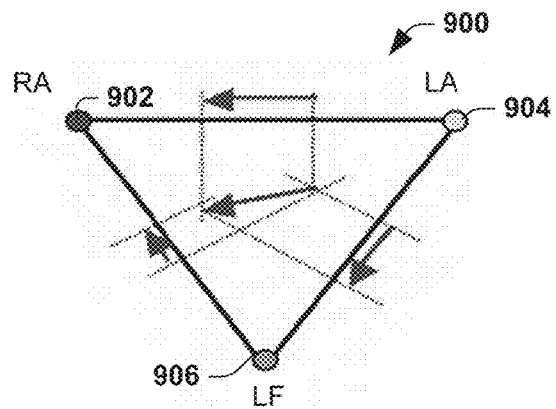
FIG. 9 depicts an example of a sensing vector that may be sensed using an implantable medical device.
Figure 10:
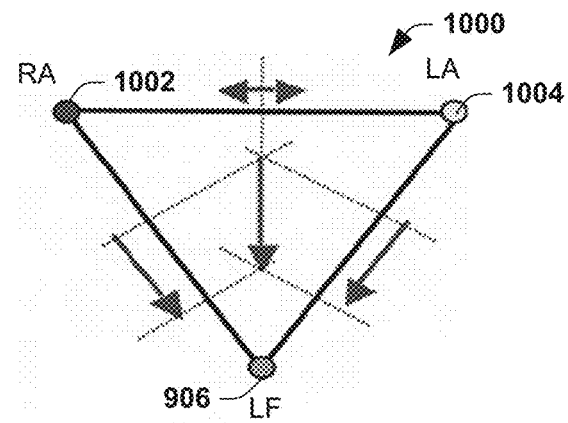
FIG. 10 depicts an example of another sensing vector that may be sensed using an implantable medical device.

By way of further example, FIGS. 9 and 10 depict examples of signal vectors 900 and 1000 that may be measured using an IMD (e.g., IMD 12, 400, 500, 600, 800) as disclosed herein. In the example of FIG. 10, sensing IMD electrodes are located at respective locations 902, 904 and 906 to provide a set of vectors, each having a magnitude and direction. For example, the signal vectors may be considered having directional components in relation to the right arm (RA), left arm (LA) and left foot (LF), respectively. The measured signal vectors in FIG. 9 thus represent distal-coil measured signal vectors for the electrode locations. In the example of FIG. 10, the signal vector also sensing IMD electrodes for electrode locations 1002, 1004 and 1006 in relation to RA, LA, and LF directions, respectively. The signal vectors shown in FIG. 10 thus represents proximal-coil measured signal vectors for the electrode locations 1002, 1004 and 1006.

Figure 11:
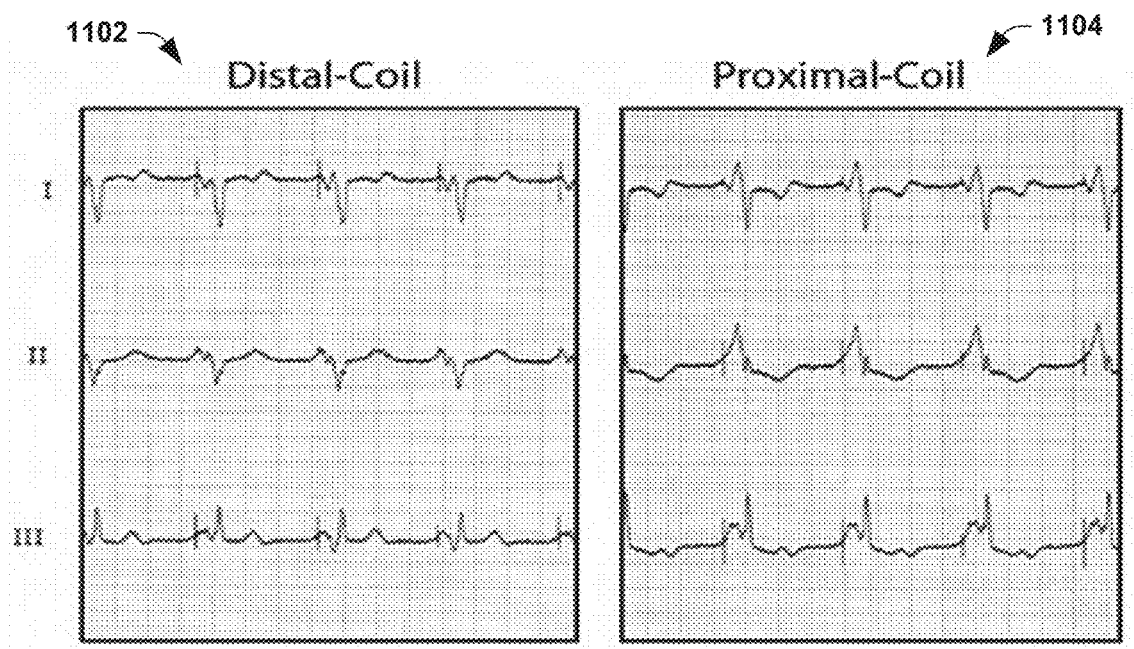
FIG. 11 depicts an example of signals corresponding to the sensing vectors of FIGS. 9 and 10.

FIG. 11 illustrates examples of measured signals 1102 and 1104 for the respective signal vectors shown in FIGS. 9 and 10. As described herein, the measured signals 1102 and 1104 may be combined with body surface signal measurements to augment electrogram reconstruction electrocardiographic mapping onto one or more surface of interest.

Figure 12:
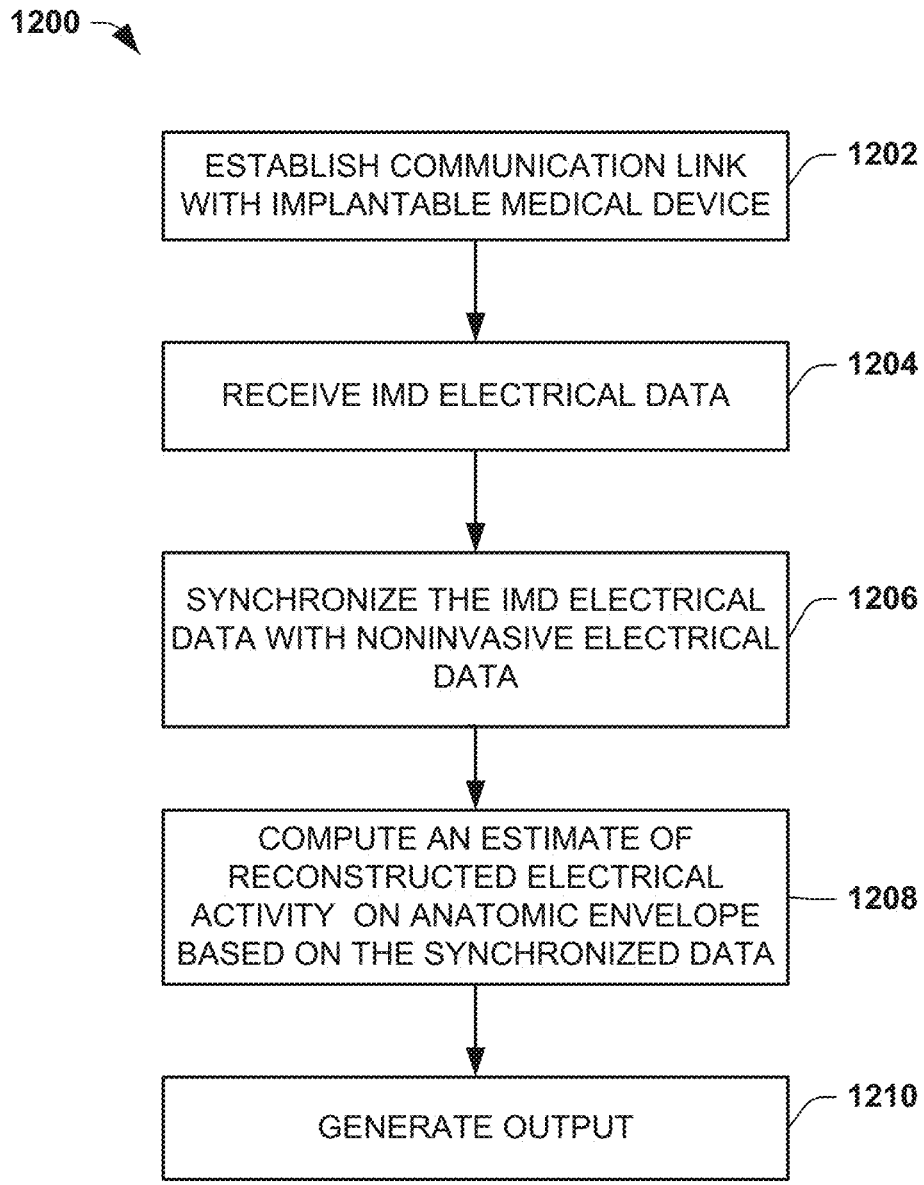
FIG. 12 is a flow diagram depicting an example of a method of using an implantable medical device to augment electrophysiology mapping.

In view of the foregoing structural and functional features described above, example methods that can be implemented will be better appreciated with reference to flow diagram of FIG. 12. While, for purposes of simplicity of explanation, the method of FIG. 12 is shown and described as executing serially, it is to be understood and appreciated that such methods are not limited by the illustrated order, as some aspects could, in other examples, occur in different orders and/or concurrently with other aspects from that disclosed herein. Moreover, not all illustrated features may be required to implement a method. The methods or portions thereof can be implemented as instructions stored in one or more non-transitory machine readable media as well as be executed by a processor of one or more computer devices, for example.

FIG. 12 depicts an example of a method 1200 to reconstruct electrical activity on surface of interest using information from an IMD. At 1202, a communications link between a noninvasive cardiac monitoring system (e.g., system 14) and an IMD (e.g., IMD 12). Useful examples of the IMD include an implantable cardioverter-defibrillator, a pacemaker or a ventricular assist device. These and similar types of devices are commercially available from Medtronic Corp and other companies. As described herein, the link may be a direct wireless connection (e.g., WiFi, Bluetooth, NFC) between the monitoring system and the IMD. In other examples, the link may be an indirect connection such as through a programmer or other device (e.g., network router or an interface device).

At 1204, the method includes receiving IMD data at the monitoring system via the communications link. For example, a communications module of the IMD encodes and sends the IMD data, which is received (directly or indirectly) by a communications module of the monitoring system. The IMD data may represent electrical signals measured by the IMD and/or signals generated by the IMD. The IMD data may also include other associated data (e.g., data identifying each electrode that provides signal measurement, time-stamps and the like). The received IMD data may be stored in memory of the monitoring system.

At 1206, the IMD electrical data is synchronized with noninvasive electrical measurement data to provide synchronized electrical data. The synchronization is performed based on timing of a synchronization signal sensed by one or more IMD electrodes and/or one or more electrodes at body surface locations. For example, the synchronization signal may be a signal pulse provided by an IMD electrode or an EP electrode, and may be a subthreshold pulse (e.g., does not create an action potential within the heart) or be a suprathreshold pulse (e.g., that creates an action potential within the heart). The noninvasive electrical data may be stored in memory representing signals generated and/or measured by body surface electrodes distributed across a surface of a patient's body, such as described herein. In one example, the synchronization at 1206 may be performed for a given measurement interval and provide a common time zero relative to which the IMD electrical data and the body surface electrical data is aligned. The synchronization may be performed once at the beginning of an analysis episode or be repeated for each subsequent measurement interval. In some examples, the synchronization may be performed periodically to resynchronize the timing and measurements of the IMD and the body surface signal measurements.

At 1208, reconstructed electrical signals are computed for locations on a surface of interest within the patient's body based on the synchronized electrical data and geometry data. The electrical data and geometry data can be stored in a non-volatile or volatile memory structure, which may be local memory to the computer executing the instructions or distributed memory (e.g., in a network or cloud system). As described, the geometry data may represent locations of the body surface EP electrodes, the location of invasive EP electrodes, the location of the IMD electrode within the patient's body and spatial configuration the surface of interest in three-dimensional space. For example, the surface of interest may be one or more surface of the heart (e.g., epicardial and/or endocardial surfaces) or any envelope between the heart and the body surface onto which the electrical signals may be reconstructed. While not shown explicitly in FIG. 12 the method 1200 may include one or more other features described herein.

In an example, the IMD includes an electrode interface (e.g., circuitry) that is coupled to one or more IMD electrodes adapted to be positioned at respective invasive locations within the patient's body. The monitoring system may be programmed to control the IMD through the communications link (e.g., directly or indirectly) to generate the synchronization signal (e.g., a pulse, such as a pacing spike) via at least one of the IMD electrodes. Electrical activity is measured by the EP electrodes (e.g., electrodes on the patient's body and/or invasive electrodes within the patient's body) responsive to the synchronization signal. The measured electrical activity is analyzed to identify a feature of the synchronization signal reflected in the measured electrical activity, and the identified feature is used to synchronize the IMD electrical data with the noninvasive electrical measurement data.

In another example, monitoring system is programmed to generate the synchronization signal via one or more EP electrodes. Electrical activity is measured by IMD electrodes within the patient's body responsive to the synchronization signal. The measured electrical activity is communicated as IMD data to the monitoring system through the communication link and analyzed to identify a feature of the synchronization signal reflected in the measured electrical activity. The identified feature is used to synchronize the IMD electrical data with the noninvasive electrical measurement data.

As yet another example, the method 1200 further includes the monitoring system controlling the IMD through the communications link to generate a calibration signal by one or more of the IMD electrodes. For example, the monitoring system generates instructions that define parameters for a calibration signal (e.g., pulse width and amplitude), and the IMD (e.g., processor) controls its signal generator to generate a calibration signal responsive to the executing the instructions from the monitoring system. The calibration signal may include one or more signals generated by one or more IMD electrodes. The electrical activity is measured by the EP electrodes (e.g., electrodes on the patient's body and/or invasive electrodes within the patient's body) responsive to the calibration signal(s). An impedance of the patient's body is determined between the IMD electrode and the electrode surface locations of the patient's body based on the measured electrical activity and the calibration signal. Model data is calibrated to characterize inhomogeneities of the patient's body between the heart and the electrode locations on the body surface based on the impedance. In some examples, a user can select a set of which inhomogeneities to include in the calibrated model data in response to a user input, which can range from using no inhomogeneities (e.g., a homogeneous model) to the most granular set of inhomogeneities. The reconstructed electrical signals may be computed at 1208 for locations on the surface of interest computed based on the calibrated model data as well as electrical measurement data (e.g., synchronized IMD data and EP data). For example, the reconstructed electrical signals may be computed by calculating a transfer matrix based on the geometry data and the calibrated model data. Regularization further may be used to compute the reconstructed electrical signals on the surface of interest based on the transfer matrix and the synchronized electrical data.

As an additional or an alternative example, the method 1200 includes determining one or more boundary conditions based on geometry data representing a location of one or more IMD electrodes together with the IMD electrical data measured by one or more respective IMD electrodes and/or IMD signals (e.g., having known signal parameters) generated by one or more respective IMD electrodes. The reconstructed electrical signals are computed on the surface of interest based on the synchronized electrical data, including electrical signals measured by the IMD electrodes and the EP electrodes, the geometry data, the at least one boundary condition being imposed to constrain computations implemented to determine the reconstructed electrical signals.

As a further additional or an alternative example, the method 1200 employs the monitoring system to control the IMD, via the communications link, to generate a stimulus signal via one or more of the IMD electrodes. For example, the stimulus signal may be delivered by a single IMD electrode or it may be delivered between one or more pairs of IMD electrodes as vector signal. In an example, a vector signal may be provided between IMD electrodes located in the same heart chamber or, in another example, in different heart chambers. The method thus may include measuring electrical activity at the surface measurement locations on the patient's body responsive to the stimulus signal, and reconstructed electrical signals are computed on the surface of interest based on the measured (synchronized) electrical activity and the geometry data.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A method comprising:
    establishing a communications link between an electrophysiology (EP) monitoring system and an implantable medical device (IMD), the IMD including an IMD processor, an IMD communications module, and an IMD electrode, in which the communications module is configured to communicate data through the communications link, the IMD electrode is implanted at a fixed location in a patient's body and coupled to the IMD processor through an electrode interface, and the EP monitoring system includes an EP processor, an EP communications module, and EP electrodes;
    controlling, by the IMD processor, the electrode interface to generate and/or measure signals at the IMD electrode;
    providing IMD electrical data to the IMD communications module, the IMD electrical data representing the signals generated and/or measured by the IMD electrode;
    receiving the IMD electrical data at the EP communications module via the communications link;
    synchronizing temporally, by the EP processor, the IMD electrical data with EP electrical measurement data to provide synchronized electrical data based on a timing feature reflected in a synchronization signal sensed by the IMD electrode and/or the EP electrodes, the EP electrical measurement data representing signals measured by the EP electrodes, and the synchronized electrical data including the IMD electrical data and the EP electrical measurement data that has been synchronized for a respective time interval; and
    computing, by the EP processor, an EP map of electrical signals for locations on a surface of interest within the patient's body based on the synchronized electrical data and geometry data, the geometry data representing locations of the EP electrodes, the location of the IMD electrode within the patient's body and geometry of the surface of interest.

2. The method of claim 1, wherein the IMD includes IMD electrodes adapted to be positioned at respective invasive locations within the patient's body, the method further comprising:
    controlling, by the EP monitoring system through the communications link, the IMD to generate the synchronization signal via at least one of the IMD electrodes;
    measuring electrical activity by the EP electrodes responsive to the synchronization signal;
    analyzing the measured electrical activity to identify the timing feature of the synchronization signal reflected in the measured electrical activity; and
    using the identified feature to synchronize the IMD electrical data with the EP electrical measurement data.

3. The method of claim 2, wherein the synchronization signal comprises a pacing spike.

4. The method of claim 1, wherein the IMD includes IMD electrodes adapted to be positioned at respective invasive locations fixed within the patient's body, the method further comprising:
    generating the synchronization signal via at least one of the EP electrodes;
    receiving IMD synchronization data at the EP communications module via the communications link, the IMD synchronization data including electrical activity measured by at least one of IMD electrodes responsive to the synchronization signal;
    analyzing the measured electrical activity of the IMD synchronization data to identify a feature of the synchronization signal; and
    using the identified feature to synchronize the IMD electrical data with the EP electrical measurement data.

5. The method of claim 1, wherein the IMD includes IMD electrodes adapted to be positioned at respective invasive locations fixed within the patient's body and the communications link is bidirectional, the method further comprising:
    controlling, by the EP monitoring system through the communications link, the IMD to generate a calibration signal by at least one of the IMD electrodes;
    measuring electrical activity by respective EP electrodes responsive to the calibration signal;

determining impedance of the patient's body between the IMD electrode and the respective EP electrodes based on the measured electrical activity and the calibration signal; and calibrating model data to characterize inhomogeneities of the patient's body between the patient's heart and an outer surface of the patient's body based on the impedance, the EP map of electrical signals for locations on the surface of interest are further computed based on the calibrated model data.

6. The method of claim 5, further comprising selecting a set of the inhomogeneities to include in the calibrated model data in response to a user input.

7. The method of claim 5, further comprising calculating a transfer matrix based on the geometry data and the calibrated model data, wherein the EP map of electrical signals are computed on the surface of interest based on the transfer matrix and the synchronized electrical data.

8. The method of claim 5, further comprising:

determining boundary condition data based on the IMD electrical data measured by at least one of the IMD electrodes and the geometry data representing the location of the respective IMD electrodes;

wherein the EP map of electrical signals are computed on the surface of interest based on the synchronized electrical data, including electrical signals measured by the IMD electrodes and the EP electrodes, the geometry data, the boundary condition data being imposed to constrain computations implemented to determine the EP map of electrical signals.

9. The method of claim 1, wherein the communications link is bidirectional, the method further comprising:

controlling the IMD, responsive to instructions received via the communications link, to deliver a stimulus signal via the IMD electrode;

storing EP electrical data for electrical activity measured by the EP electrodes over a respective time interval responsive to the stimulus signal; and wherein the EP map of electrical signals is computed on the surface of interest based on the stored EP electrical data and the geometry data.

10. The method of claim 9, wherein controlling the IMD further comprises controlling the IMD to deliver the stimulus signal to include respective pulses of varying frequencies and/or frequency content over time, wherein the EP map of electrical signals is computed to assess transthoracic inhomogeneities responsive to the stimulus signal.

11. The method of claim 1, wherein the communications link comprises a first link between the EP monitoring system and a programmer and a second link between the programmer and the IMD, and wherein at least the second link is a wireless link.

12. The method of claim 1, wherein the IMD comprises a cardioverter-defibrillator, a pacemaker or a ventricular assist device.

13. A method comprising:

establishing a bidirectional communications link between an electrophysiology (EP) monitoring system and an implantable medical device (IMD), the IMD including an IMD processor, an IMD communications module, and a plurality of IMD electrodes at respective fixed locations within a patient's body, in which the IMD electrodes are coupled to the IMD processor through an electrode interface and the communications module is configured to communicate data through a communications link;

receiving IMD electrical data at the EP monitoring system via the communications link, the IMD electrical data representing signals generated and/or measured by at least one of the IMD electrodes;

synchronizing the IMD electrical data with EP electrical measurement data to provide synchronized electrical data based on timing of a synchronization signal sensed by each of the IMD electrodes and/or by EP electrodes of the EP monitoring system, the EP electrical measurement data representing signals measured by the EP electrodes;

controlling the IMD, responsive to instructions received from the EP monitoring system via the communications link, to provide a vector signal from one of the IMD electrodes to at least one other of the IMD electrodes;

measuring electrical activity by the EP electrodes at measurement locations on an outer surface of the patient's body over a respective time interval responsive to the vector signal; and generating an EP map of electrical signals on the surface of interest based on the measured electrical activity over the respective time interval, the vector signal and geometry data, the geometry data representing locations of the EP electrodes, respective locations of the IMD electrodes within the patient's body and the surface of interest.

14. The method of claim 13, wherein the EP electrodes include an arrangement of body surface electrodes configured to measure body surface electrical activity and store body surface electrical measurement data representing signals measured by the body surface electrodes responsive to the stimulus signal, wherein generating the EP map comprises:

reconstructing electrical signals on the surface of interest based on the body surface electrical measurement data, the IMD electrical data and the geometry data, wherein the EP map is generated based on the reconstructed electrical signals and the IMD electrical data to provide respective global and local assessments of cardiac tissue responsive to the stimulus signal.

15. The method of claim 13, further comprising:

controlling the IMD, responsive to instructions received from the EP monitoring system via the communications link, to provide a series of vector signals from different ones of the IMD electrodes; and measuring electrical activity by the EP electrodes at the measurement locations responsive to the series of vector signals; and generating one or more EP maps of electrical signals on the surface of interest based on the electrical activity measured by the EP electrodes for the series of vector signals and the geometry data.

16. A system comprising:

an implantable medical device (IMD) comprising an IMD processor, a first communications module, an electrode interface and an IMD electrode adapted to be positioned at a fixed location within a patient's body, in which the IMD electrode is coupled to the IMD processor through the electrode interface configured to provide IMD electrical data based on an electrical signal sensed by the IMD electrode and to control delivery of a stimulus signal through the IMD electrode; and an electrophysiology (EP) monitoring system comprising:
EP electrodes;
a second communications module;
non-transitory memory to store the IMD electrical data, EP electrical data and geometry data, the EP electrical data representing signals measured by the EP electrodes;
an EP processor coupled to the memory to access data and instructions stored in the memory, and coupled to the second communications module, the instructions programmed to at least:
establish a communications link between the first and second communications modules while the IMD electrode is implanted at the fixed location in the patient's body;
receive the IMD electrical data through the communications link;
synchronize the IMD electrical data and the EP electrical data to provide synchronized electrical data based on a timing feature reflected in a synchronization signal sensed by the IMD electrode and/or the EP electrodes, the synchronized electrical data including electrical signals measured by the IMD electrodes and the EP electrodes that has been synchronized for a respective time interval; and
compute a map of electrical signals for locations residing on a surface of interest based on the synchronized electrical data and the geometry data, the geometry data representing locations of the EP electrodes, the location of the IMD electrode within the patient's body and geometry of the surface of interest.

17. The system of claim 16, at least some of the EP electrodes of the EP monitoring system comprising a non-invasive sensor apparatus including respective EP electrodes, the sensor apparatus configured to position the respective electrodes on the surface of the patient's body.

18. The system of claim 16, further comprising a programmer device having a third communications module, the third communications module of the programmer device configured to communicate with the first communications module of the IMD over a first communication link, and configured to communicate with the second communications module of the EP monitoring system over a second communications link.

19. The system of claim 16, wherein the IMD includes a plurality of IMD electrodes adapted to be positioned at respective fixed locations within the patient's body and the instructions are further programmed to:
send program instructions to the IMD over the communications link to control the IMD to generate the synchronization signal via at least one of the IMD electrodes;
store electrical signal data measured by the EP electrodes responsive to the synchronization signal; and
analyze the stored electrical signal data to identify the timing feature of the synchronization signal reflected in the electrical signal data, the IMD electrical data and the EP electrical data being synchronized based on the identified feature.

20. The system of claim 16, wherein the IMD includes a plurality of IMD electrodes adapted to be positioned at respective fixed locations within the patient's body and the instructions are further programmed to:
generate the synchronization signal via at least one of the EP electrodes;
receive IMD synchronization data via the communications link, the IMD synchronization data representing electrical activity measured by at least one of IMD electrodes responsive to the synchronization signal; and
analyze the measured electrical activity of the IMD synchronization data to identify the timing feature of the synchronization signal, the IMD electrical data and the EP electrical data being synchronized based on the identified feature.

21. The system of claim 16, wherein the IMD includes a plurality of IMD electrodes adapted to be positioned at respective fixed locations within the patient's body and the instructions are further programmed to:
control the IMD to generate a calibration signal by at least one of the IMD electrodes;
measure electrical activity between respective pairs of the electrodes responsive to the calibration signal;
determine impedance of the patient's body between the respective pairs of the electrodes based on the measured electrical activity and the calibration signal; and
calibrate model data to characterize inhomogeneities of the patient's body between the patient's heart and the surface of the patient's body based on the impedance, the EP map of electrical signals for locations on the surface of interest are computed also based on the calibrated model data.

22. The system of claim 21, wherein the EP electrodes include respective body surface electrodes distributed across a surface of the patient's body, wherein the instructions are further programmed to:
calculate a transfer matrix based on the geometry data and the calibrated model data,
wherein the EP map of electrical signals comprises a map reconstructed electrical signals on the surface of interest based on the transfer matrix and the synchronized electrical data.

23. The system of claim 16, wherein the instructions are further programmed to:
determine boundary condition data based on the IMD electrical data measured by the IMD electrode and the geometry data representing a location of the IMD electrode;
wherein the EP map of electrical signals are computed on the surface of interest based on the geometry data and the synchronized electrical data, the synchronized electrical data including electrical signals measured by the IMD electrodes and the EP electrodes, wherein the boundary condition data is imposed to constrain computations implemented to determine the EP map of electrical signals.

24. The system of claim 16, wherein the instructions are further programmed to:
control the IMD, via the communications link, to generate the stimulus signal via the IMD electrode; and
store EP electrical data for electrical activity measured by the EP electrodes responsive to the stimulus signal,
wherein the EP map of electrical signals are computed on the surface of interest based on the stored EP electrical data and the geometry data.

25. The system of claim 24, wherein the instructions are further programmed to:
control the IMD to deliver the stimulus signal to include respective pulses of varying frequencies and/or frequency content over time, wherein the EP map of electrical signals is computed to assess transthoracic inhomogeneities responsive to the stimulus signal.

26. The system of claim 16, wherein the IMD includes a plurality of electrodes at respective locations represented by the geometry data, wherein the instructions are further programmed to:
- control the IMD, via the communications link, to generate a vector signal from one of the IMD electrodes to at least one other of the IMD electrodes;
- store EP electrical data for electrical activity measured by the EP electrodes responsive to the vector signal;
- wherein the EP map of electrical signals are computed on the surface of interest based on the stored EP electrical data, the vector signal and the geometry data.

27. The system of claim 26, wherein the EP electrodes comprise an arrangement of body surface electrodes configured to measure body surface electrical activity and body surface electrical measurement data is stored in the memory to represent signals measured by the body surface electrodes responsive to the stimulus signal, wherein computing the EP map of electrical signals comprises:
- reconstructing electrical signals on the surface of interest for based on the EP electrical data, including the body surface electrical activity, the IMD electrical data and the geometry data, wherein the EP map of electrical signals includes the reconstructed electrical signals and signals represented by the IMD electrical data to provide respective global and local assessments of cardiac tissue.

28. The system of claim 27, wherein the IMD electrodes further comprise one or more electrodes configured to measure invasive electrophysiology signals concurrently with non-invasive measurements by the body surface electrodes.

\* \* \* \* \*